United States Patent
Kuo et al.

(10) Patent No.: US 6,780,994 B2
(45) Date of Patent: Aug. 24, 2004

(54) PHTHALIMIDO ARYLPIPERAZINES USEFUL IN THE TREATMENT OF BENIGN PROSTATIC HYPERPLASIA

(75) Inventors: Gee-Hong Kuo, Scotch Plains, NJ (US); William V. Murray, Belle Mead, NJ (US); Catherine P. Prouty, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/207,473

(22) Filed: Jul. 29, 2002

(65) Prior Publication Data

US 2003/0088099 A1 May 8, 2003

Related U.S. Application Data

(62) Division of application No. 10/014,979, filed on Dec. 11, 2001, now abandoned, which is a division of application No. 09/489,744, filed on Jan. 21, 2000, now Pat. No. 6,362,338, which is a division of application No. 09/251,143, filed on Feb. 17, 1999, now Pat. No. 6,063,785.
(60) Provisional application No. 60/075,510, filed on Feb. 20, 1998.

(51) Int. Cl.[7] ............................................. C07D 295/13
(52) U.S. Cl. ....................................................... 544/394
(58) Field of Search ........................................ 544/394

(56) References Cited

U.S. PATENT DOCUMENTS

| | | | |
|---|---|---|---|
| 3,920,707 A | | 11/1975 | Descamps et al. |
| 5,244,901 A | * | 9/1993 | George et al. ............... 514/252 |
| 5,545,645 A | * | 8/1996 | Pascal et al. ............... 514/326 |

FOREIGN PATENT DOCUMENTS

| | | |
|---|---|---|
| EP | 0 522 915 A | 1/1993 |
| GB | 1 470 039 A | 4/1977 |
| HU | 167137 B | 8/1974 |
| HU | 174113 B | 11/1979 |
| HU | 177702 B | 3/1981 |
| WO | WO 86 04901 A | 8/1986 |
| WO | WO 98 51298 A | 11/1998 |

OTHER PUBLICATIONS

"Protective Groups in Organic Chemistry" J.F.W.McOmie (Editor), p. 61–63 (1973).*
Gutcait, A. et al: "Studies on Quinazolines. 6. Assymettric Synthesis of (S)–(+)– and (R)–(–)–3–((4–(2–methoxyphenyl)piperazin–1–yl)methyl)–5–methylthio–2,3–dihydro-imidaz o(1,2–c)quinazolines"; Tetrahedron: Assymmetry; 1996, pp. 1641–1648, vol. 7, No. 6; XP002105739; Oxford, GB.
Kuo, G. et al: "Phtalimido Arylpeperazines As Alpha 1A Receptor Antagonists Useful in the Treatment of Benign Prostatic HyperPlasia"; PCT International Search Report, Jun. 14, 1999; WIPO International Bureau.
Hungarian Search Report Application No. P0100704 dated Sep. 16, 2002.

* cited by examiner

Primary Examiner—Emily Bernhardt
(74) Attorney, Agent, or Firm—Laura A. Donnelly

(57) ABSTRACT

This invention relates to a series of heterocyclic substituted piperazines of Formula I pharmaceutical compositions containing them and intermediates used in their manufacture. The compounds of the invention selectively inhibit binding to the $\alpha\text{-}1_a$ adrenergic receptor, a receptor which has been implicated in benign prostatic hyperplasia. As such the compounds are potentially useful in the treatment of this disease.

3 Claims, 2 Drawing Sheets

Effects of Compound 21 upon IUP and MAP at 10 µg/kg PE in dogs

Effects of Compound 46 upon IUP and MAP at 10 µg/kg PE in dogs

Duration Studies Compound 21

Duration Studies Compound 21

PHTHALIMIDO ARYLPIPERAZINES USEFUL IN THE TREATMENT OF BENIGN PROSTATIC HYPERPLASIA

This is a divisional application of a U.S. patent application Ser. No. 10/014,979, filed on Dec. 11, 2001 now abandoned; which is a divisional application of U.S. patent application Ser. No. 09/489,744 filed Nov. 21, 2000, now issued as U.S. Pat. No. 6,362,338, which is a divisional application of U.S. Ser. No. 09/251,143 filed on Feb. 17, 1999, now issued as U.S. Pat. No. 6,063,785, which is a non-provisional application which claims priority of U.S. Provisional Patent Application Serial No. 60/075,510, filed on Feb. 20, 1998.

FIELD OF THE INVENTION

This invention relates to a series of phthalimido arylpiperazine derivatives, pharmaceutical compositions containing them as well as processes and intermediates used in their manufacture. The compounds of the invention selectively inhibit binding to the $\alpha 1_a$ adrenergic receptor, a receptor which has been implicated in benign prostatic hyperplasia. As such the compounds are potentially useful in the treatment of this disease.

BACKGROUND

Benign prostatic hyperplasia (BPH), a nonmalignant enlargement of the prostate, is the most common benign tumor in men. Approximately 50% of all men older than 65 years have some degree of BPH and a third of these men have clinical symptoms consistent with bladder outlet obstruction (Hieble and Caine, 1986). In the U.S., benign and malignant diseases of the prostate are responsible for more surgery than diseases of any other organ in men over the age of fifty.

There are two components of BPH, a static and a dynamic component. The static component is due to enlargement of the prostate gland, which may result in compression of the urethra and obstruction to the flow of urine from the bladder. The dynamic component is due to increased smooth muscle tone of the bladder neck and the prostate itself (which interferes with emptying of the bladder) and is regulated by alpha 1 adrenergic receptors ($\alpha$1-ARs). The medical treatments available for BPH address these components to varying degrees, and the therapeutic choices are expanding.

Surgical treatment options address the static component of BPH and include transurethral resection of the prostate (TURP), transurethral incision of the prostate (TUIP), open prostatectomy, balloon dilatation, hyperthermia, stents and laser ablation. TURP is the preferred treatment for patients with BPH and approximately 320,000 TURPs were performed in the U.S. in 1990 at an estimated cost of $2.2 billion (Weis et al., 1993). Although an effective treatment for most men with symptomatic BPH, approximately 20–25% of patients do not have a satisfactory long-term outcome (Lepor and Rigaud, 1990). Complications include retrograde ejaculation (70–75% of patients), impotence (5–10%), postoperative urinary tract infection (5–10%), and some degree of urinary incontinence (2–4%) (Mebust et al., 1989). Furthermore, the rate of reoperation is approximately 15–20% in men evaluated for 10 years or longer (Wennberg et al., 1987).

Apart from surgical approaches, there are some drug therapies which address the static component of this condition. Finasteride (Proscar, Merck), is one such therapy which is indicated for the treatment of symptomatic BPH. This drug is a competitive inhibitor of the enzyme 5$\alpha$-reductase which is responsible for the conversion of testosterone to dihydrotestosterone in the prostate gland (Gormley et al., 1992). Dihydrotestosterone appears to be the major mitogen for prostate growth, and agents which inhibit 5$\alpha$-reductase reduce the size of the prostate and improve urine flow through the prostatic urethra. Although finasteride is a potent 5$\alpha$-reductase inhibitor and causes a marked decrease in serum and tissue concentrations of dihydrotestosterone, it is only moderately effective in treating symptomatic BPH (Oesterling, 1995). The effects of finasteride take 6–12 months to become evident and for many men the clinical improvement is minimal (Barry, 1997).

The dynamic component of BPH has been addressed by the use of adrenergic receptor blocking agents ($\alpha$1-AR blockers) which act by decreasing the smooth muscle tone within the prostate gland itself. A variety of $\alpha$1-AR blockers (terazosin, prazosin, and doxazosin) have been investigated for the treatment of symptomatic bladder outlet obstruction due to BPH, with terazosin (Hytrin, Abbott) being the most extensively studied. Although the $\alpha$1-AR blockers are well-tolerated, approximately 10–15% of patients develop a clinically adverse event (Lepor, 1995). The undesirable effects of all members of this class are similar, with postural hypotension being the most commonly experienced side effect (Lepor et al., 1992). In comparison to the 5$\alpha$-reductase inhibitors, the $\alpha$1-AR blocking agents have a more rapid onset of action (Steers, 1995). However, their therapeutic effect, as measured by improvement in the symptom score and the peak urinary flow rate, is moderate. (Oesterling, 1995)

The use of $\alpha$1-AR antagonists in the treatment of BPH is related to their ability to decrease the tone of prostatic smooth muscle, leading to relief of the obstructive symptoms. Adrenergic receptors are found throughout the body play a dominant role in the control of blood pressure, nasal congestion, prostrate function and other processes (Harrison et al., 1991). However, there are a number of cloned $\alpha$1-AR receptor subtypes: $\alpha 1_a$-AR, $\alpha 1_b$-AR and $\alpha 1_d$-AR (Bruno et al., 1991; Forray et al., 1994; Hirasawa et al., 1993; Ramarao et al., 1992; Schwinn et al., 1995; Weinberg et al., 1994). A number of labs have characterized the $\alpha$1-ARs in human prostate by functional, radioligand binding, and molecular biological techniques (Forray et al., 1994; Hatano et al., 1994; Marshall et al., 1992; Marshall et al., 1995; Yamada et al., 1994). These studies provide evidence in support of the concept that the $\alpha 1_a$-AR subtype comprises the majority of $\alpha$1-ARs in human prostatic smooth muscle and mediates contraction in this tissue. These findings suggest that the development of a subtype-selective $\alpha 1_a$-AR antagonist might result in a therapeutically effective agent with reduced side effects for the treatment of BPH.

SUMMARY OF THE INVENTION

The compounds of this invention selectively bind to the $\alpha 1_a$-AR receptor, antagonize the activity of said receptor and are selective for prostate tissue over aortic tissue. As such, these represent a viable treatment for BHP without the side effects associated with known α1-AR antagonists.

The invention includes compounds of Formula I

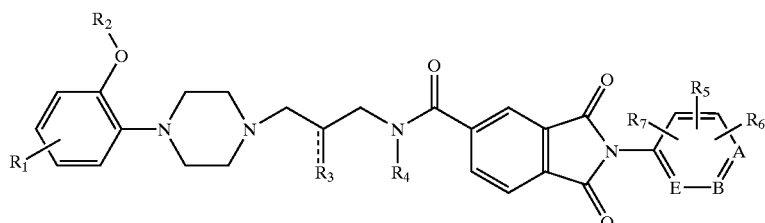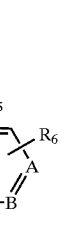

I wherein:
$R_1$ is hydrogen, halogen, $C_{1-5}$alkoxy, hydroxyl, or $C_{1-5}$alkyl;
$R_2$ is $C_{1-6}$alkyl, substituted $C_{1-6}$alkyl
  where the alkyl substituents are independently selected from one or more halogens,
  phenyl,
  substituted phenyl
    where the phenyl substituents are independently selected from one or more members of the group consisting of $C_{1-5}$alkyl, $C_{1-5}$alkoxy, and trihalo$C_{1-5}$alkyl,
  phenyl$C_{1-5}$alkyl, or
  substituted phenyl$C_{1-5}$alkyl
    where the phenyl substituents are independently selected from one or more members of the group consisting of $C_{1-5}$alkyl, halogen, $C_{1-5}$alkoxy, and trihalo$C_{1-5}$alkyl;
$R_3$ is hydrogen, hydroxy or $C_{1-5}$alkoxy if the hashed line is absent or is oxygen if the hashed line is present;
$R_4$ is hydrogen, $C_{1-5}$alkyl, phenyl$C_{1-5}$alkyl or substituted phenyl$C_{1-5}$alkyl
  where the phenyl substitutents are independently selected from one or more members of the group consisting of $C_{1-5}$alkyl, $C_{1-5}$alkoxy, and trihalo$C_{1-5}$alkyl;
$R_5$ is hydrogen, halogen, hydroxy, $C_{1-8}$alkyl, substituted $C_{1-8}$alkyl
  where the alkyl substitutents are independently selected from one or more halogens,
  $C_{1-5}$alkoxy, amino, $C_{1-5}$alkylamino, di$C_{1-5}$alkylamino, $C_{1-5}$alkylcarbonyl, $C_{1-5}$alkoxycarbonyl, nitrile, or nitro;
$R_6$ is hydrogen, halogen, hydroxy, $C_{1-8}$alkyl, substituted $C_{1-8}$alkyl
  where the alkyl substitutents are independently selected from one or more halogens,
  $C_{1-5}$alkoxy, amino, $C_{1-5}$alkylamino, di$C_{1-5}$alkylamino, $C_{1-5}$alkylcarbonyl, $C_{1-5}$alkoxycarbonyl, or nitro;
$R_7$ is hydrogen, halogen, hydroxy, $C_{1-8}$alkyl, substituted $C_{1-8}$alkyl
  where the alkyl substitutents are independently selected from one or more halogens,
  $C_{1-5}$alkoxy, amino, $C_{1-5}$alkylamino, di$C_{1-5}$alkylamino, $C_{1-5}$alkylcarbonyl, $C_{1-5}$alkoxycarbonyl, or nitro;
A is nitrogen or carbon;
B is nitrogen or carbon;
E is nitrogen or carbon;
with the proviso that only one of A, B, or E is nitrogen;
pharmaceutically acceptable salts thereof; and
stereoisomers, racemic mixtures, as well as enantiomers thereof.

In addition this invention contemplates pharmaceutical compositions containing an effective dose of compounds of Formula I. Still further this invention contemplates methods of treating diseases associated with the α1$_a$ adrenergic receptor consisting of administering an effective dose of a compound of Formula I to a mammal. This invention also contemplates a method of treating benign prostatic hyperplasia consisting of administering an effective dose of a compound of Formula I to a mammal.

Aside from compounds of Formula I, this invention contemplates intermediate compounds of Formula II and Formula III. These intermediates are useful in the preparation of compounds of Formula I and are as follows:

Formula II

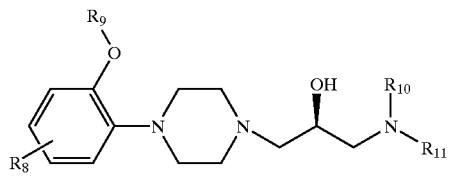

wherein
$R_8$ is hydrogen, halogen, $C_{1-5}$alkoxy, hydroxyl, or $C_{1-5}$alkyl;
$R_9$ is $C_{1-6}$alkyl, substituted $C_{1-6}$alkyl
  where the alkyl substituents are independently selected from one or more halogens,
  phenyl,
  substituted phenyl
    where the phenyl substituents are independently selected from one or more members of the group consisting of $C_{1-5}$alkyl, $C_{1-5}$alkoxy, and trihalo$C_{1-5}$alkyl,
  phenyl$C_{1-5}$alkyl, or
  substituted phenyl$C_{1-5}$alkyl
    where the phenyl substituents are independently selected from one or more members of the group consisting of $C_{1-5}$alkyl, halogen, $C_{1-5}$alkoxy, and trihalo$C_{1-5}$alkyl;
$R_{10}$ is hydrogen, $C_{1-5}$alkoxycarbonyl, phenyl$C_{1-5}$alkoxycarbonyl or allyloxycarbonyl;
$R_{11}$ is hydrogen, phenyl$C_{1-5}$alkyl, or substituted phenyl$C_{1-5}$alkyl
  where the phenyl substituents are independently selected from one or more members of the group consisting of $C_{1-5}$alkyl, halogen, $C_{1-5}$alkoxy, and nitro;

Formula III

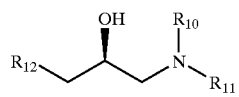

wherein
$R_{10}$ is $C_{1-5}$alkoxycarbonyl, phenyl$C_{1-5}$alkoxycarbonyl, or allyloxycarbonyl;

$R_{11}$ is phenyl$C_{1-5}$alkyl, or substituted phenyl$C_{1-5}$alkyl
  where the phenyl substituents are independently selected from one or more members of the group consisting of $C_{1-5}$alkyl, halogen, $C_{1-5}$alkoxy, and nitro;
$R_{12}$ is halogen, mesyl, tosyl, or hydroxy.

Still further the invention contemplates methods of making compounds of Formula II. Those methods are as follows:
Reacting a compound of Formula III

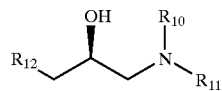

III wherein
$R_{10}$ is $C_{1-5}$alkoxycarbonyl, phenyl$C_{1-5}$alkoxycarbonyl, or allyloxycarbonyl;
$R_{11}$ is phenyl$C_{1-5}$alkyl, or substituted phenyl$C_{1-5}$alkyl
  where the phenyl substituents are independently selected from one or more members of the group consisting of $C_{1-5}$alkyl, halogen, $C_{1-5}$alkoxy, and nitro;
$R_{12}$ is halogen, mesyl, tosyl, or hydroxy.
with a piperazine derivative of Formula IV

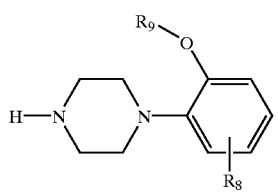

IV wherein
$R_8$ is hydrogen, halogen, $C_{1-5}$alkoxy, hydroxyl, or $C_{1-5}$alkyl;
$R_9$ is $C_{1-6}$alkyl, substituted $C_{1-6}$alkyl
  where the alkyl substituents are independently selected from one or more halogens,
  phenyl,
  substituted phenyl
    where the phenyl substituents are independently selected from one or more members of the group consisting of $C_{1-5}$alkyl, $C_{1-5}$alkoxy, and trihalo$C_{1-5}$alkyl,
  phenyl$C_{1-5}$alkyl, or
  substituted phenyl$C_{1-5}$alkyl
    where the phenyl substituents are independently selected from one or more members of the group consisting of $C_{1-5}$alkyl, halogen, $C_{1-5}$alkoxy, and trihalo$C_{1-5}$alkyl;
in the presence of a basic reagent to produce a compound for Formula II

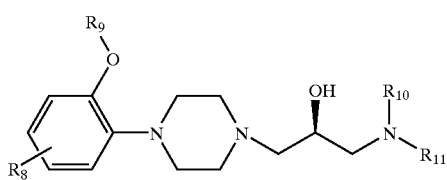

II wherein
$R_8$ is hydrogen, halogen, $C_{1-5}$alkoxy, hydroxyl, or $C_{1-5}$alkyl;
$R_9$ is $C_{1-6}$alkyl, substituted $C_{1-6}$alkyl
  where the alkyl substituents are independently selected from one or more halogens,
  phenyl,
  substituted phenyl
    where the phenyl substituents are independently selected from one or more members of the group consisting of $C_{1-5}$alkyl, $C_{1-5}$alkoxy, and trihalo$C_{1-5}$alkyl,
  phenyl$C_{1-5}$alkyl, or
  substituted phenyl$C_{1-5}$alkyl
    where the phenyl substituents are independently selected from one or more members of the group consisting of $C_{1-5}$alkyl, halogen, $C_{1-5}$alkoxy, and trihalo$C_{1-5}$alkyl;
$R_{10}$ is $C_{1-5}$alkoxycarbonyl, phenyl$C_{1-5}$alkoxycarbonyl, or allyloxycarbonyl;
$R_{11}$ is phenyl$C_{1-5}$alkyl, or substituted phenyl$C_{1-5}$alkyl
  where the phenyl substituents are independently selected from one or more members of the group consisting of $C_{1-5}$alkyl, halogen, $C_{1-5}$alkoxy, and nitro;
Reacting a compound of Formula II

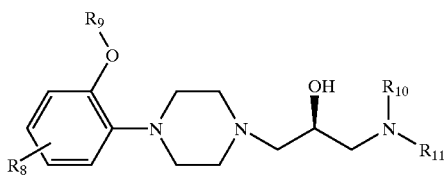

II wherein
$R_8$ is hydrogen, halogen, $C_{1-5}$alkoxy, hydroxyl, or $C_{1-5}$alkyl;
$R_9$ is $C_{1-6}$alkyl, substituted $C_{1-6}$alkyl
  where the alkyl substituents are independently selected from one or more halogens,
  phenyl,
  substituted phenyl
    where the phenyl substituents are independently selected from one or more members of the group consisting of $C_{1-5}$alkyl, $C_{1-5}$alkoxy, and trihalo$C_{1-5}$alkyl,
  phenyl$C_{1-5}$alkyl, or
  substituted phenyl$C_{1-5}$alkyl
    where the phenyl substituents are independently selected from one or more members of the group consisting of $C_{1-5}$alkyl, halogen, $C_{1-5}$alkoxy, and trihalo$C_{1-5}$alkyl;
$R_{10}$ is $C_{1-5}$alkoxycarbonyl, phenyl$C_{1-5}$alkoxycarbonyl, or allyloxycarbonyl;
$R_{11}$ is phenyl$C_{1-5}$alkyl, or substituted phenyl$C_{1-5}$alkyl
  where the phenyl substituents are independently selected from one or more members of the group consisting of $C_{1-5}$alkyl, $C_{1-5}$alkoxy, and nitro; with an acidic reagent to give a compound of Formula II

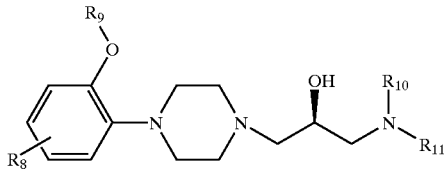

II wherein
$R_8$ is hydrogen, halogen, $C_{1-5}$alkoxy, hydroxyl, or $C_{1-5}$alkyl;
$R_9$ is $C_{1-6}$alkyl, substituted $C_{1-6}$alkyl
  where the alkyl substituents are independently selected from one or more halogens,
  phenyl,
  substituted phenyl
    where the phenyl substituents are independently selected from one or more members of the group consisting of $C_{1-5}$alkyl, $C_{1-5}$alkoxy, and trihalo$C_{1-5}$alkyl, phenylC$_{1-5}$alkyl, or
substituted phenylC$_{1-5}$alkyl
  where the phenyl substituents are independently selected from one or more members of the group consisting of C$_{1-5}$alkyl, halogen, C$_{1-5}$alkoxy, and trihaloC$_{1-5}$alkyl;
R$_{10}$ is hydrogen
R$_{11}$ is phenylC$_{1-5}$alkyl, or substituted phenylC$_{1-5}$alkyl
  where the phenyl substituents are independently selected from one or more members of the group consisting of C$_{1-5}$alkyl, halogen, C$_{1-5}$alkoxy, and nitro;
Reacting a compound of Formula II

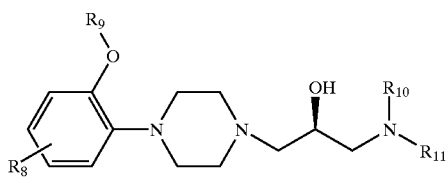

II wherein
R$_8$ is hydrogen, halogen, C$_{1-5}$alkoxy, hydroxyl, or C$_{1-5}$alkyl;
R$_9$ is C$_{1-6}$alkyl, substituted C$_{1-6}$alkyl
  where the alkyl substituents are independently selected from one or more halogens,
  phenyl,
  substituted phenyl
    where the phenyl substituents are independently selected from one or more members of the group consisting of C$_{1-5}$alkyl, C$_{1-5}$alkoxy, and trihaloC$_{1-5}$alkyl,
  phenylC$_{1-5}$alkyl, or
  substituted phenylC$_{1-5}$alkyl
    where the phenyl substituents are independently selected from one or more members of the group consisting of C$_{1-5}$alkyl, halogen, C$_{1-5}$alkoxy, and trihaloC$_{1-5}$alkyl;
R$_{10}$ is hydrogen
R$_{11}$ is phenylC$_{1-5}$alkyl, or substituted phenylC$_{1-5}$alkyl
  where the phenyl substituents are independently selected from one or more members of the group consisting of C$_{1-5}$alkyl, halogen, C$_{1-5}$alkoxy, and nitro;
with a reducing agent to give a compound of Formula II

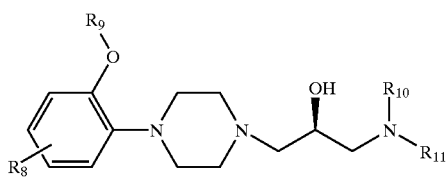

II wherein
R$_8$ is hydrogen, halogen, C$_{1-5}$alkoxy, hydroxyl, or C$_{1-5}$alkyl;
R$_9$ is C$_{1-6}$alkyl, substituted C$_{1-6}$alkyl
  where the alkyl substituents are independently selected from one or more halogens,
  phenyl,
  substituted phenyl
    where the phenyl substituents are independently selected from one or more members of the group consisting of C$_{1-5}$alkyl, C$_{1-5}$alkoxy, and trihaloC$_{1-5}$alkyl,
  phenylC$_{1-5}$alkyl, or
  substituted phenylC$_{1-5}$alkyl
    where the phenyl substituents are independently selected from one or more members of the group consisting of C$_{1-5}$alkyl, halogen, C$_{1-5}$alkoxy, and trihaloC$_{1-5}$alkyl;
R$_{10}$ is hydrogen;
R$_{11}$ is hydrogen;

DETAILED DESCRIPTION OF THE INVENTION

Figure 1:
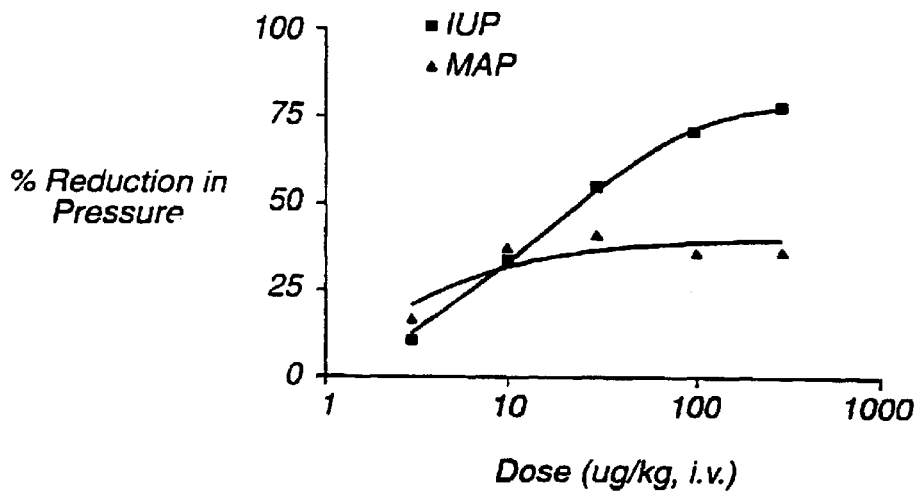
FIG. 1 is a graph of the effects of Compound 21 on the reduction of IUP and MAP responses in dogs.

The terms used in describing the invention are commonly used and known to those skilled in the art. However, the terms that could have other meanings are defined. "HBSS" refers to Hank's Balanced Salt Solution. "Independently" means that when there are more than one substituent, the substitutents may be different. The term "alkyl" refers to straight, cyclic and branched-chain alkyl groups and "alkoxy" refers to O-alkyl where alkyl is as defined supra. "DMAP" refers to dimethylaminopyridine, "TFA" refers to trifluoroacetic acid, "HOBT" refers to hydroxybenzotriazole hydrate, "HATU" refers to O-(7-azabenzotriazol-1-yl)-1,1,3,3-tetrametyluronium hexafluorophosphate, and "EDCl" refers to 1-(3-dimethylaminopropyl)-3-ethylcarbodiimide hydrochloride. The symbol "Ph" refers to phenyl, and "aryl" includes mono and fused aromatic rings such as phenyl and naphthyl. The symbol "CPDA" refers to 1,1-cyclopentanediacetimid-1-yl and "IID" refers to 1H-isoindole 1,3-(2H)dion-1-yl. The symbol "ES" refers to electrospray and the symbol "MS" refers to mass spectrum. Some of the compounds of Formula I include a chiral carbon atom. Therefore those compounds may be prepared as stereoisomers, racemic mixtures or pure enantiomers. All stereoisomers, pure enantiomers and racemic mixtures are considered to be within the scope of this invention.

The compounds of the invention may be prepared by the following schemes, where some schemes produce more than one embodiment of the invention. In those cases, the choice of scheme is a matter of discretion which is within the capabilities of synthetic chemists.

A compound of Formula I where A, B, and E are carbon, R$_1$ is hydrogen, R$_2$ is phenyl, R$_3$ is hydroxy, R$_4$ is hydrogen, and R$_5$ is 3-trifluoromethyl may be prepared using Scheme 1. The scheme assembles two halves of the desired molecule and couples them together using peptide coupling reagents. One half is prepared by treating 1,2,4-benzenetricarboxylic anhydride, 1a, with a substituted aniline derivative, 1b, at about 130° C. in an acidic solvent such as glacial acetic acid for about 16–24 h to give the carboxy substituted phthalimido derivative 1c. The other half is prepared in two steps. First, 1-azido-3-(p-toluenesulfonyloxy)propan-2-ol 1d, is heated at about 100° C. with an appropriately substituted piperazine derivative, 1e for about 2–5 days to give the azide 1f. This azide is treated with Pd/C and H$_2$ (50 psi) in an inert solvent over 16 h to give the free amine 1q. This amine is treated with 1c, HOBT, DMAP, EDCl, and N,N'-diisopropylethylamine in methylene chloride at about room temperature for 2-6 h to give the desired compound of Formula I. Alternatively, 1c and 1q may be coupled using other peptide coupling agents such as HATU and DMAP. This scheme may be used to prepare a number of compounds of Formula I. For example, if compounds where A, B or E is nitrogen are desired, replace 1b with an amino pyridine derivative such as 2-aminopyridine and follow the remaining steps of the scheme. To prepare compounds where R$_1$ and R$_2$ vary, simply replace the illustrated 1e with any known substituted piperazines. Although the illustrated product was prepared from the racemic azide 1d, the pure enantiomers of this azide are known and can be used in this scheme.

Compounds where $R_3$ is carbonyl may be prepared by treating the products of Scheme 1 with an oxidizing agent such as the Swern's reagent (formed with oxalyl chloride and DMSO) at $-78°$ C. to room temperature over 30 min to 1 h.

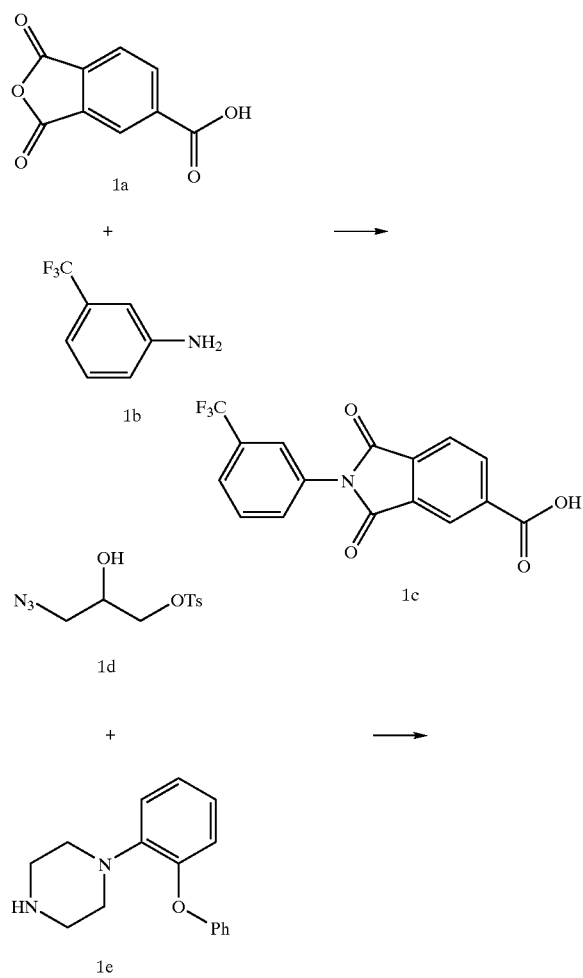

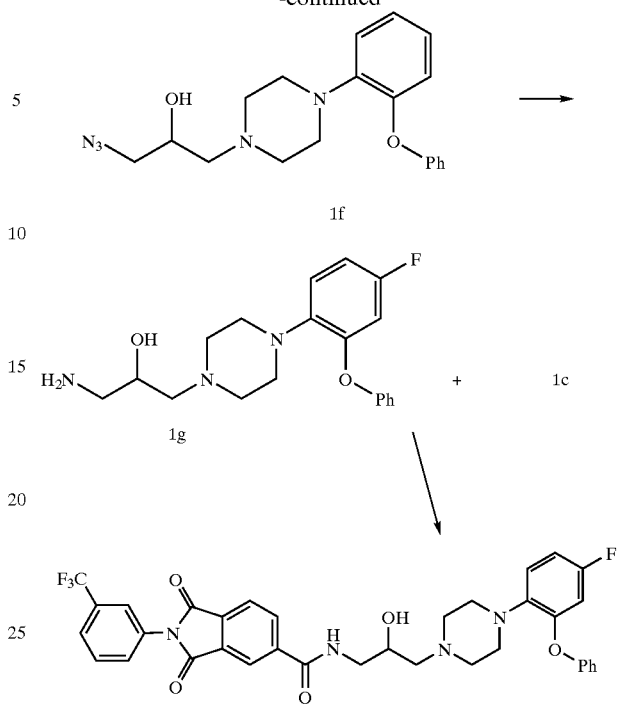

Scheme 2 may be used to prepare compounds of Formula I where A is nitrogen, $R_1$ is fluoro, $R_2$ is ethyl, $R_3$ is hydrogen, $R_4$ is hydrogen, and $R_5$ is hydrogen. Treatment of 1,2,4-benzenetricarboxylic anhydride, 2a, with the aniline derivative, 2b gives the phthalimide 2c. An appropriately substituted piperazine derivative 2d is treated with the N-BOC protected 3-bromopropylamine and cesium carbonate in acetonitrile at reflux for 16 h to give the substituted piperazine derivative 2f. This derivative is converted to the free amine, 2g, by treatment with TFA and methylene chloride at room temperature over 2-6 h. Derivatives 2g and 2c were coupled using HOBT, DMAP, EDCl, and N,N'-diisopropylethylamine in methylene chloride at about room temperature for 2-6 h to give the desired compound of Formula 1. As described in Scheme 1, Scheme 2 may be modified to give all of the compounds of Formula I.

Scheme 2

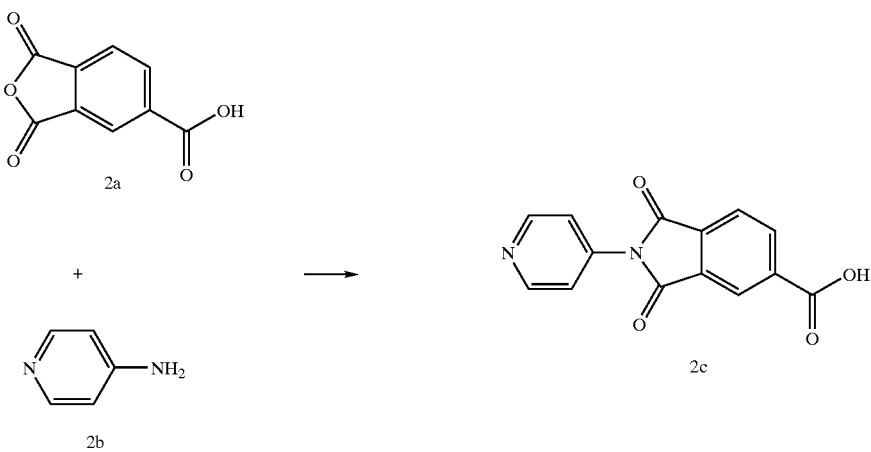

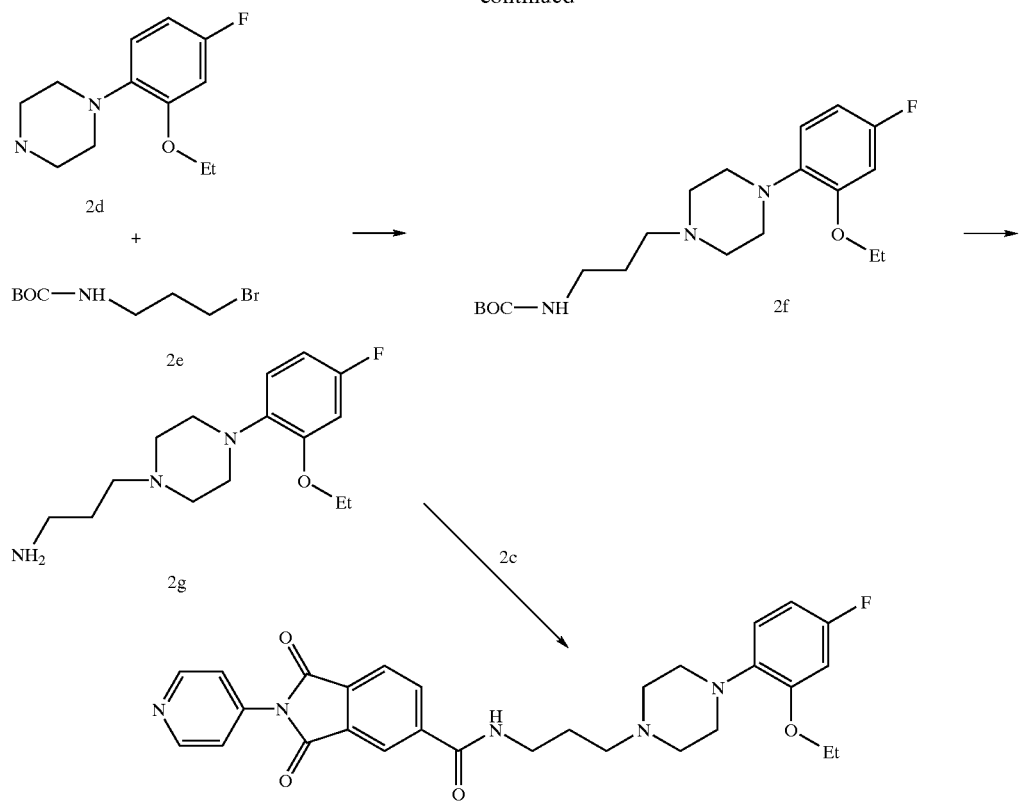

To produce compounds of the invention where $R_4$ is other than hydrogen, Scheme 3 may be used. The amino group of intermediate 2g may be treated with an aldehyde 3a such as benzaldehyde to give the imine 3b. This intermediate may be reduce with $NaBH_4$ at room temperature to give the monoamine 3c. This amine is coupled with a substituted phthalimide derivative, 2c using HATU, DMAP and diisopropylethylamine in methylene chloride at about room temperature for 2-6 h to give the desired compound of Formula I. As described in previous schemes, Scheme 3 may be modified to give a number of compounds of Formula I. For example, to produce a compound where $R_3$ is hydroxy, replace 2g with intermediate 1g and follow the remaining steps of Scheme 3.

Scheme 3

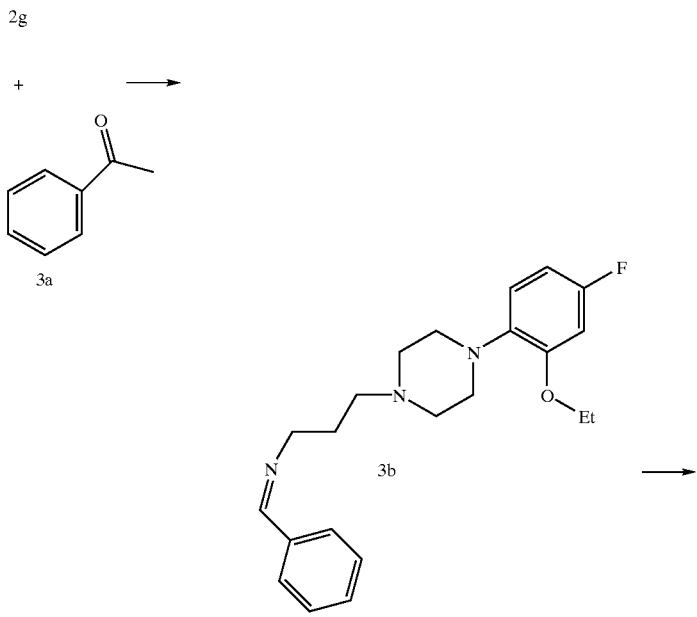

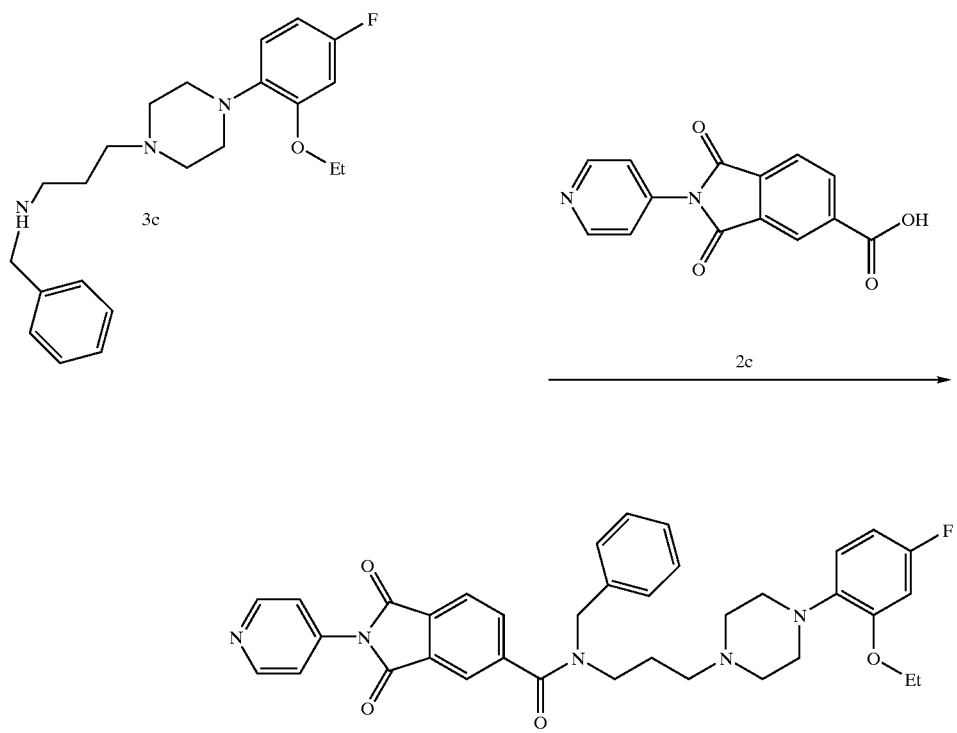

To produce compounds of the invention where $R_3$ is $C_{1-5}$alkoxy, Scheme 4 may be used. Treatment of the azido derivative 1d with an appropriately substituted piperazine, such as 4a at about 100° C. for about 2–5 days gives intermediate 4b. This intermediate is treated with two equivalents of a strong organic base, such as sodium hydride in an inert solvent, such as THF, at 0° C. for about 1-5 h; followed by treatment with an additional equivalent of base and an alkylating agent such as ethyl iodide, at 0° C. for about 1-5 h to give the ether 4c. This ether is treated with Pd/C and $H_2$ (ca. 50 psi) in an inert solvent over 16 h to give the free amine 4d. This amine is coupled with a phthalimido derivative such as 4e with HATU and DMAP to give the desired compounds of the invention. As discussed in schemes 1-3, scheme 4 may be modified in a like manner to give all of the compounds of Formula I.

Scheme 4

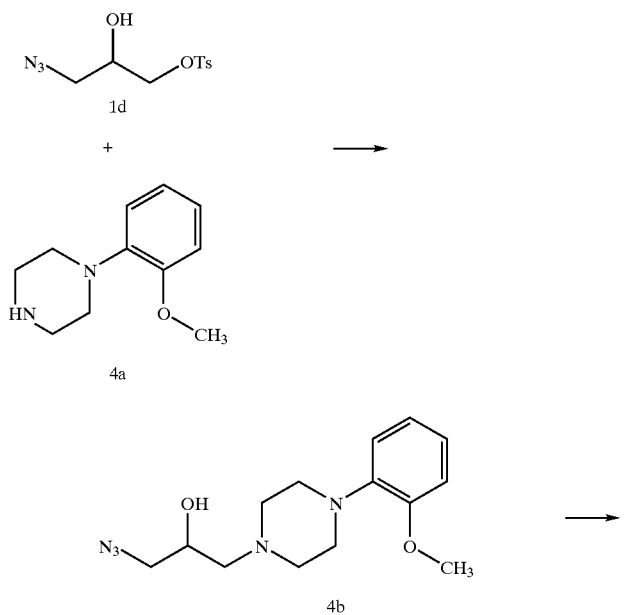

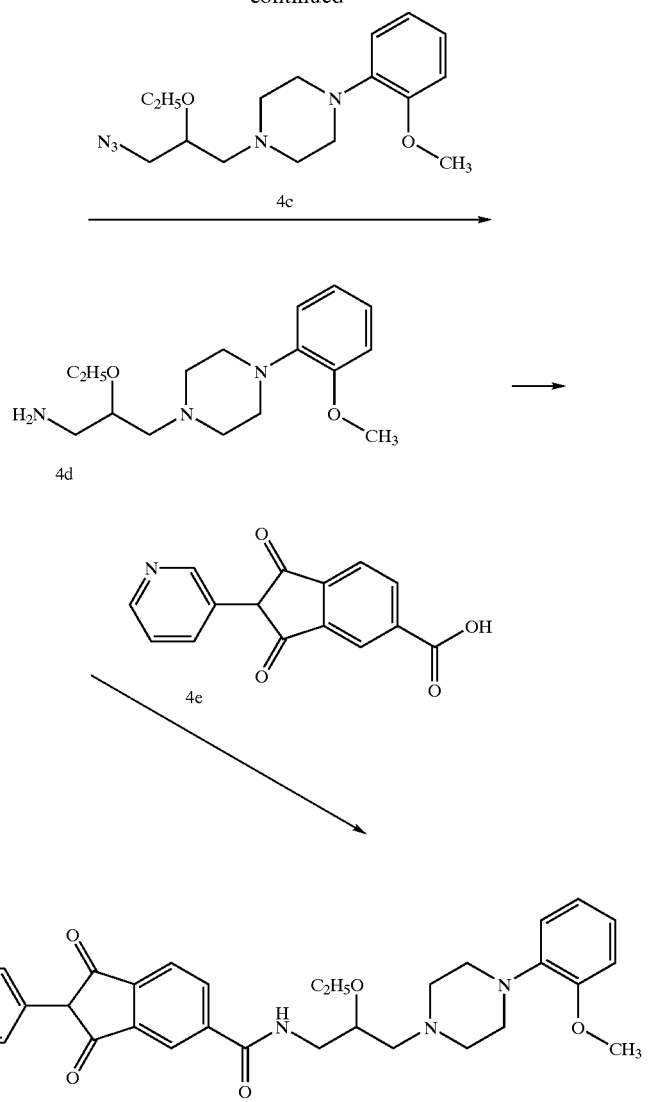

To produce pure enantiomers of compounds of Formula I where R₃ is hydroxy, Scheme 5 may be used. (S)(+) epichlorohydrin (97% ee) may be treated with benzylamine in a suitable organic solvent such as hexane at about room temperature for about 48–72 hours to give hydroxy compound 5a. This intermediate may be treated with a BOC reagent agent such as di-tert-butyl dicarbonate, and an organic base such as triethylamine in an inert solvent such as THF at about 0° C. to about room temperature over 10 to 24 h to give the N-protected derivative 5b. This intermediate may be treated with piperazine derivative, 5c, a basic reagents, such as potassium hydroxide, sodium hydroxide, or lithium hydroxide, in an alcoholic solvent such as methanol at about 0° C. to about room temperature over about 1 to about 3 days to give the coupled derivative 5d. This compound may be deprotected by treatment with an acidic reagents, such as TFA or 1-6N HCl, at about room temperature over 18-24 h to give free amine 5e. This amine may be debenzylated with using a reducing agents, such as palladium catalyst and ammonium formate, sodium in liquid ammonia, or palladium and hydrogen, in an alcoholic solvent such as EtOH at about 45–60° C. over 20 h to give the primary amine 5f. This amine may be coupled to acids of type 5g using peptide coupling agents such as HATU to give a compound of Formula I. As described in Scheme I, Scheme 5 may be modified to give a number of compounds of Formula I.

Scheme 5

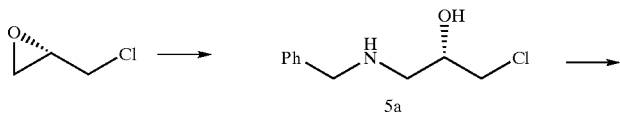

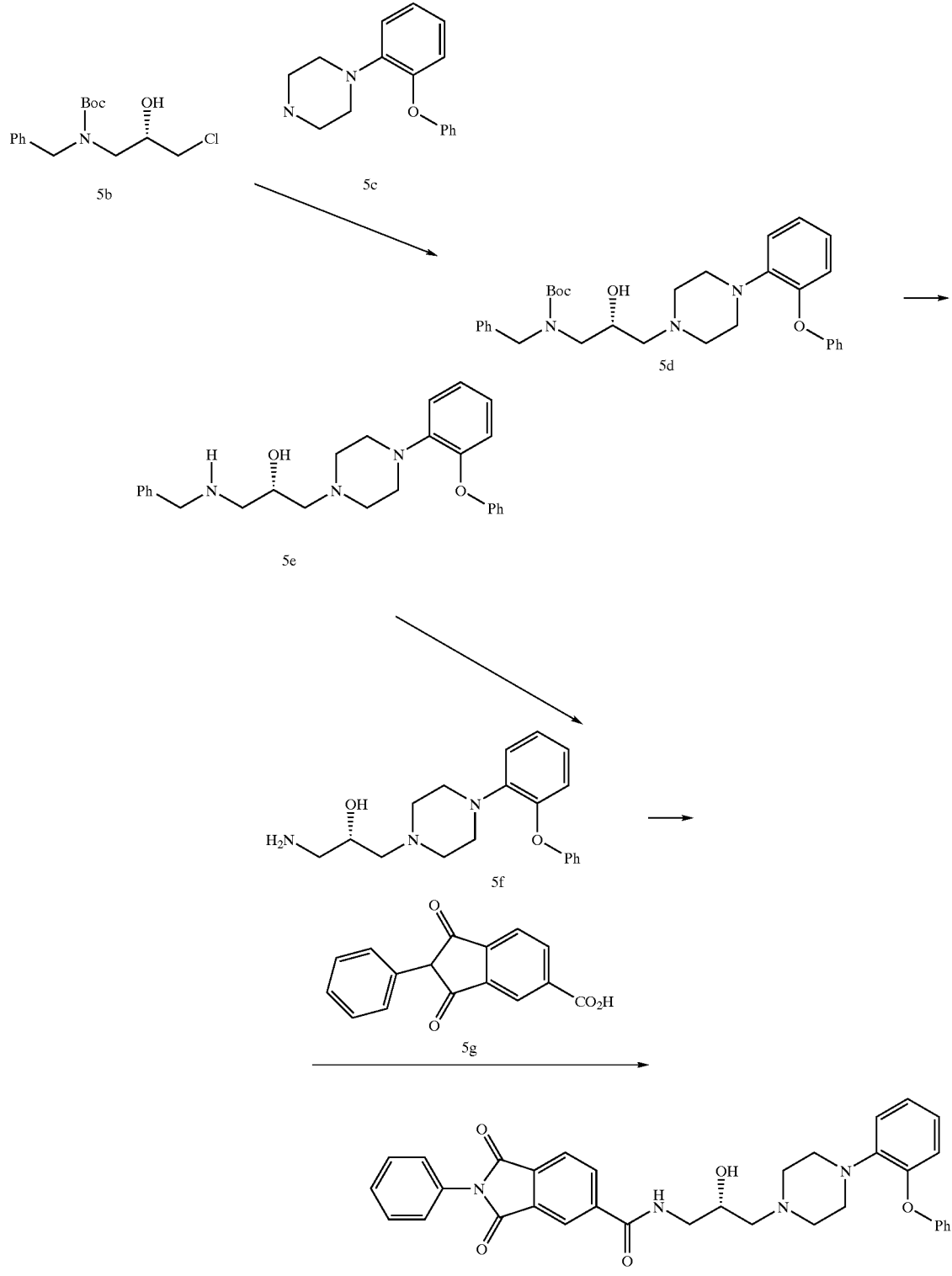

Although the claimed compounds are useful as antagonists of α1$_a$-AR, some compounds are more active than others and are either preferred or particularly preferred. The preferred compounds of Formula I include:

$R_1$ is halogen or hydroxy,
$R_2$ is phenylC$_{1-5}$alkyl or hydrogen,
$R_3$ is C$_{1-5}$alkoxy,
$R_4$ is C$_{1-5}$alkyl,
$R_5$, $R_6$, and $R_7$ are independently selected from hydrogen, nitrile and amino,
A is nitrogen or carbon,
B is carbon, and
C is carbon.

The particularly preferred compounds of Formula I include compounds where:

$R_1$ is hydrogen, $R_2$ is $C_{1-6}$alkyl, phenyl or substituted phenyl, $R_3$ is hydrogen, hydroxy, $R_4$ is hydrogen, $R_5$, $R_6$, and $R_7$ are independently selected from halogen, hydrogen, hydroxy, $C_{1-8}$alkyl, $C_{1-5}$alkoxy, and $diC_{1-5}$ alkylamino, A is carbon, B is carbon, and E is carbon.

The preferred compounds of Formula II include compound where $R_8$ is hydrogen, $R_9$ is $C_{1-6}$alkyl, $R_{10}$ is hydrogen, $C_{1-5}$alkoxycarbonyl, phenyl$C_{1-5}$alkoxycarbonyl, and $R_{11}$ is hydrogen, phenyl$C_{1-5}$alkyl, or $C_{1-5}$alkoxy substituted phenyl.

The particularly preferred compounds of Formula II include compounds where $R_8$ is hydrogen, $R_9$ is isopropyl, $R_{10}$ is hydrogen, t-butoxycarbonyl, benzyloxycarbonyl, and $R_{11}$ is hydrogen, benzyl.

The preferred compounds of Formula III include compound where $R_{10}$ is $C_{1-5}$alkoxycarbonyl, $R_{11}$ is phenyl$C_{1-5}$alkyl, or $C_{1-5}$alkoxy substituted phenyl, and $R_{12}$ is hydrogen or halogen.

The particularly preferred compounds of Formula III include compounds where $R_{10}$ is t-butoxycarbonyl $R_{11}$ is benzyl, and $R_{12}$ is chlorine.

The preferred basic reagent for producing a compound of Formula II is potassium hydroxide. The preferred acidic reagent for treating a compound of Formula III is trifluoroacetic acid. The preferred reducing agent for treating a compound of Formula II is ammonium formate and Pd/C.

As indicated by the biological activity, the compounds of Formula I may be used in pharmaceutical compositions to treat patients (humans and other primates) with disorders related to inhibiting the activity of the $\alpha 1_a$ adrenergic receptor. The preferred route is oral administration, however compounds may be administered by intravenous infusion. Oral doses range from about 0.01 to about 100 mg/kg daily; where the optimal dose range is about 0.1 to about 25 mg/kg/per day. Infusion doses can range from about 0.001–1 mg/kg/min of inhibitor, admixed with a pharmaceutical carrier over a period ranging from several minutes to several days.

The pharmaceutical compositions can be prepared using conventional pharmaceutical excipients and compounding techniques. Oral dosage forms may be elixers, syrups, capsules tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated and used as free bases, however the compounds may be isolated and used as their pharmaceutically acceptable salts. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic.

In order to illustrate the invention the following examples are included. These examples do not limit the invention. They are meant only to suggest a method of practicing the invention. Those skilled in the art may find other methods of practicing the invention, which are obvious to them. However those methods are deemed to be within the scope of this invention.

PREPARATIVE EXAMPLES

Example 1

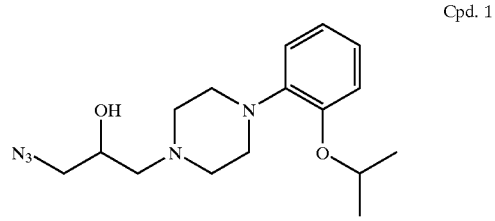

Cpd. 1

The fumarate salt of 1-(2-isopropoxyphenyl)-piperazine (3.91 g, 12 mmol) was basified with 20% NaOH$_{(aq)}$ (100 mL) and extracted with methylene chloride. The combined organic layers were dried (Na$_2$SO$_4$) and concentrated to give an oil (2.74 g). A mixture of the oil and 1-azido-3-(p-toluenesulfonyloxy)propan-2-ol (3.25 g, 12 mmol, Antonin Holy, Collect. Czech. Chem. Comm. 1989, 54(2), 446) was stirred at 100° C. for 36 h. The cooled mixture was diluted with water and extracted with ether, dried (Na$_2$SO$_4$) and concentrated. The product was purified by column chromatography (SiO$_2$) to yield compound 1 as (2.92 g, 76%) as a light-brown solid: MS (ES) m/z: 320 (MH$^+$); Anal. Calcd for C16H25N5O2:C, 60.17; H, 7.89; N, 21.93. Found: C, 60.45; H, 7.83; N, 22.01.

Example 2

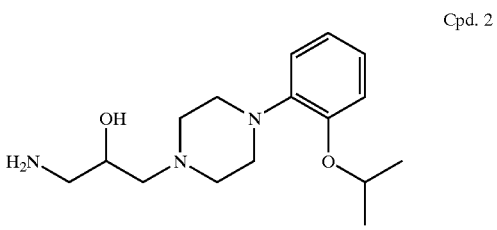

Cpd. 2

10% HCl (6 mL) was added to a mixture of compound 1 (2.43 g, 7.6 mmol) and 10% Pd/C (1.22 g) in MeOH (60 mL) and the mixture was hydrogenated under H$_2$ (50 psi) in a Parr shaker for 16 h at 20° C. The mixture was filtered through celite and the filtrate was concentrated. The residue was basified with 20% NaOH and extracted with methylene chloride. The combined organic layers were dried ($Na_2SO_4$) and concentrated to yield compound 2 as a yellowish oil (2.2 g, 95%): MS (ES) m/z: 294 ($MH^+$)

Example 3

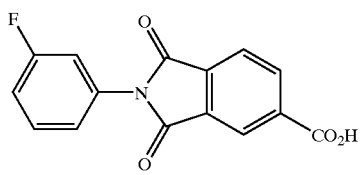

Cpd. 3

A mixture of the 1,2,4-benzenetricarboxylic anhydride (10 g, 52 mmol) and 3-fluoroaniline (5.77 g, 52 mmol) in glacial acidic acid (200 mL) was stirred at 130° C. for 16 h. The light-brown solution was cooled to 20° C. to give a yellow solid precipitate. The yellow solid was collected via filtration and was washed thoroughly with water to remove the trace amount of acetic acid. The product was dried at 60° C. for 36 h under vacuum to yield a yellow solid (11.41 g, 77%): MS (ES) m/z: 284 ($MH^+$).

Example 4

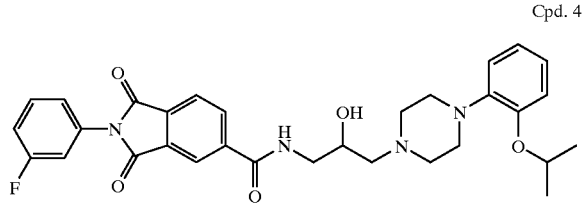

Cpd. 4

A mixture of compound 2 (226 mg, 0.77 mmol), compound 3 (220 mg, 0.77 mmol), EDCl (151 mg, 0.78 mmol), HOBT (105 mg, 0.78 mmol), DMAP (cat.) and N,N-diisopropylethylamine (0.52 mL) in methylene chloride (6 mL) was stirred at 20° C. for 3 h. The mixture was concentrated, diluted with water and extracted with EtOAc. The combined organic layer was dried ($Na_2SO_4$), concentrated. The product was purified by column chromatography ($SiO_2$) and further recrystallized from EtOAc/Hexane to yield compound 4 (101 mg, 23%) as a yellow solid: $^1$H NMR (300 MHz, $CDCl_3$) δ8.34 (s, 1H), 8.30 (d, J=7.8 Hz, 1H), 8.04 (d, J=7.8 Hz, 1H), 7.48 (m, 1H), 7.26 (m, 1H), 7.14 (m, 1H), 6.91 (m, 6H), 4.59 (m, 1H), 4.02 (m, 1H), 3.79 (m, 1H), 3.45 (m, 1H), 3.13 (m, 4H), 2.87 (m, 2H), 2.62 (m, 2H), 2.50 (m, 2H), 1.34 (d, J=6.0 Hz, 6H); MS (ES) m/z: 561 ($MH^+$).

Example 5

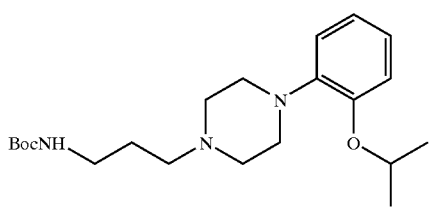

Cpd. 5

3-Bromopropylamine hydrobromide (5 g, 22.8 mmol) was dissolved in 10% NaOH (50 mL), extracted with methylene chloride and concentrated. To the free base in methylene chloride was added $(Boc)_2O$ (5.23 g, 23.9 mmol) and this mixture was stirred at 20° C. for 4 h. The methylene chloride layer was washed with $H_2O$, diluted citric acid (6%), $NaHCO_3$ and sat NaCl solution, dried and concentrated. The product was purified by column chromatography ($SiO_2$) to yield the protected amine (4.84 g, 89%). The fumarate salt of 1-(2-isopropoxyphenyl)-piperazine (5.1 g, 15 mmol) was basified with 20% $NaOH_{(aq)}$ (100 mL), extracted with methylene chloride, dried ($Na_2SO_4$) and concentrated to give a yellow oil (3.15 g). A mixture of the oil, the protected amine (3.42 g, 14.3 mmol), and $Cs_2CO_3$ (4.66 g, 14.3 mmol) in $CH_3CN$ (50 mL) was heated at reflux overnight. Solid was filtered off and the filtrate was evaporated. The product was purified by column chromatography ($SiO_2$) to yield compound 5(4.4 g, 81%): MS (ES) m/z: 378($MH^+$)

Example 6

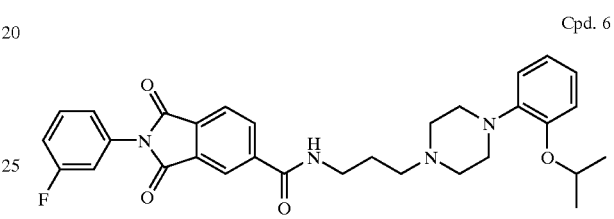

Cpd. 6

Compound 5 (3.97 g, 11.4 mmol) was dissolved in 25% TFA/methylene chloride (50 mL). The reaction was stirred at RT for 5 h, the solvent was evaporated and solid residue was obtained. This solid was dissolved in 20% NaOH (aq) (100 mL) and stirred for 40 min. Then the free base was extracted into methylene chloride (3×). A light yellow oil was obtained (3.0 g, 95%). A solution of this free amine (3.0 g, 10.8 mmol) and diisopropylethyl amine (5.6 g, 43.3 mmol) in methylene chloride (80 mL) was added to a mixture containing EDCl (2.08 g, 10.8 mmol) HOBT (1.46 g, 10.8 mmol), catalytic amount of DMAP and compound 3 (3.09 g, 10.8 mmol). Reaction was stirred overnight at 20° C. under $N_2$. The reaction mixture was washed with water (3×). The product was purified by column chromatography ($SiO_2$) to yield compound 6 (1.34 g, 23%): $^1$H NMR (300 MHz, $CDCl_3$) δ8.34 (m, 2H), 7.99 (d, J=8.1 Hz, 1H), 7.46 (q, J=8.0, 6.4 Hz, 1H), 7.18 (m, 2H), 6.89 (m, 4H), 4.57 (q, J=12.0, 6.0 Hz, 1H), 3.67(m, 2H), 3.09 (brs, 4H), 2.71 (m, 6H), 1.87 (m, 2H), 1.33 (d, J=6.1 Hz, 6H); MS (ES) m/z: 545 ($MH^+$). Anal. Calc'd for $C_{31}H_{33}FN_4O_4$: C, 68.37; H, 6.11; N, 10.29. Found: C, 68.13; H, 6.10; N, 10.17

Example 7

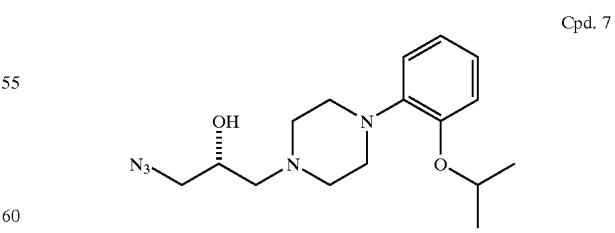

Cpd. 7

The fumarate salt of 1-(2-isopropoxyphenyl)-piperazine (112.5 g, 345 mmol) was basified with 20% $NaOH_{(aq)}$ (500 mL) and extracted with methylene chloride (3×). The combined organic extracts were dried ($Na_2SO_4$) and concentrated to give about 70 g oil. A mixture of the oil and (2S)-3-azido-2-hydroxypropyl p-toluenesulfonate (91 g, 335 mmol, Kristina Juricova, *Collect. Czech. Chem. Comm.* 1995, 60, 237) was stirred at 100° C. in NMP in the presence of triethylamine (70 g, 690 mmol) for 30 h. The cooled mixture was diluted with water and extracted with ether (3×500 mL), back washed once with NaCl (sat) (100 mL), dried (Na$_2$SO$_4$) and concentrated. The product was purified by column chromatography (SiO$_2$) to yield compound 7 (70.6 g, 66%) (98.8% ee assay by chiralcel AD column) as a off-white solid after recrystallization from methylene chloride/hexane:

$[\alpha]_D^{25}$-3.6° (c=1, CH$_{30}$H); $^1$H NMR (300 MHz, CDCl$_3$) δ6.91 (m, 4H), 4.59 (m,1H), 3.93 (m,1H), 3.67 (brs,1H), 3.42 (dd, J=12.6, 3.8 Hz, 1H), 3.23 (dd, J=12.6, 5.4 Hz, 1H), 3.12 (m, 4H), 2.83 (m, 2H), 2.53 (m, 3H), 2.42 (dd, J=12.2, 3.8 Hz, 1H), 1.34 (d, J=6.0 Hz, 6H); MS (ES)m/z: 320 (MH$^+$)

Example 8

Cpd. 8

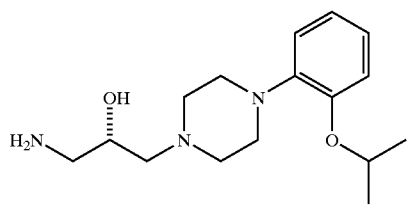

10% HCl (6 mL) was added to a mixture of compound 7 (15 g, 47 mmol) and 10% Pd/C (4 g) in MeOH (100 mL) and the mixture was hydrogenated under H$_2$ (50 psi) in a Parr shaker for 21 h at 20° C. The resulting mixture was filtered through celite and the filtrate was concentrated. The residue was basified with 20% NaOH$_{(aq)}$ (75 mL) and extracted with methylene chloride (3×), dried (Na$_2$SO$_4$) and concentrated to yield compound 8 as a yellowish oil (14 g, ~100%): $[a]_D^{25}$+23.6° (c=1, CHCl$_3$); $^1$H NMR (300 MHz, CDCl$_3$) δ6.91 (m, 4H), 4.59 (m, 1H), 3.76 (m,1H), 3.12 (m, 4H), 2.83 (dd, J=12.7, 3.7 Hz, 2, H), 2.82 (m, 1H), 2.25–2.68 (m, 8H), 1.34 (d, J=6.1 Hz, 6H); MS (ES) m/z: 294 (MH$^+$)

Example 9

Cpd. 9

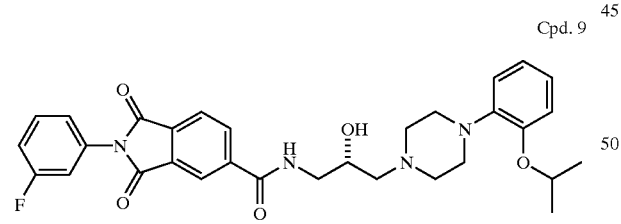

Compound 8 (1 g, 3.41 mmol) was dissolved in a mixture of diisopropylethyl amine (2.3 mL, 13.6 mmol) and methylene chloride (10 mL). To the above light-yellowish solution was added compound 3 (970 mg, 3.4 mmol) and HATU (1.296 g, 3.41 mmol) and stirred at 20° C. for 18 h, concentrated. 10% K$_2$CO$_3$ (aq) was added and the mixture was extracted with ether (3×), dried (Na$_2$SO$_4$), and concentrated. The product was purified by column chromatography (SiO$_2$, EtOAc/Hexane then methylene chloride/Acetone) to give an a oily solid. The product was further recrystallized from EtOAc/hexane to give compound 9 as a yellow solid (830 mg, 43%): $[\alpha]_D^{25}$+8.3° (c=1, CHCl$_3$); $^1$H NMR (300 MHz, CDCl$_3$) δ8.34 (s, 1H), 8.30 (d, J=7.8 Hz, 1H), 8.04 (d, J=7.8 Hz, 1H), 7.48 (m, 1H), 7.26 (m, 1H), 7.14 (m, 1H), 6.91 (m, 6H), 4.59 (m, 1H), 4.02 (m, 1H), 3.79 (m, 1H), 3.45 (m, 1H), 3.13 (m, 4H), 2.87 (m, 2H), 2.62 (m, 2H), 2.50 (m, 2H), 1.34 (d, J=6.0 Hz, 6H); MS (ES) m/z: 561(MH$^+$).

Example 10

Cpd. 10

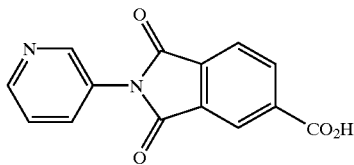

A mixture of the 1,2,4-benzenetricarboxylic anhydride (2 g, 10.4 mmol), and 3-aminopyridine (0.98 g, 10.4 mmol) in glacial acidic acid (40 mL) was stirred at 130° C. for 16 h. The mixture was cooled and the white solid was filtered off and was washed with water. The product was dried for 24 h under vacuum to yield compound 10 as a white solid (2.55 g, 91%): MS (ES) m/z: 267 (MH$^+$).

Example 11

Cpd. 11

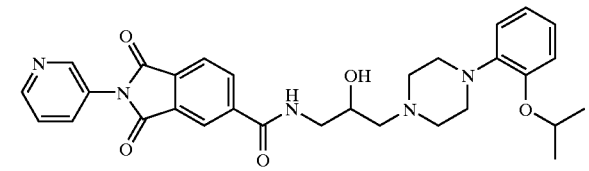

A mixture of compound 2 (0.2 g, 0.68 mmol), EDCl (132 mg, 0.68 mmol), HOBT (94 mg, 0.68 mmol), DMAP (cat.), compound 10 (0.18 g, 0.68 mmol) and N,N-diisopropylethylamine (0.46 mL, 2.72 mmol) in methylene chloride (6 mL) was stirred at 20° C. overnight. The mixture was concentrated and purified by column chromatography (SiO$_2$, methylene chloride/acetone=10:1 to 1:1) to yield compound 11 as a solid (67 mg, 18%):MS (ES) m/z: 544(MH$^+$).

Example 12

Cpd. 12

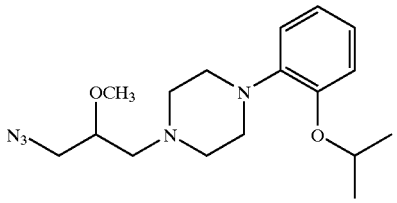

Compound 1 (0.8 g, 2.5 mmol) was dissolved in anhydrous THF (50 mL). The solution was cooled to 0° C. and 60% NaH (0.2 g, 5.0 mmol) was added. The solution was stirred for 10 min and CH$_3$I (0.53 g, 3.8 mmol) was added. The reaction mixture was stirred at 0° C. for 2 h, NaH (0.1 g, 2.5 mmol) and CH$_3$I (0.15 mL) were added and this mixture was stirred for another 2 h. The reaction was quenched with sat NH$_4$Cl, the solvent was evaporated and the aqueous layer was washed with methylene chloride (3×), dried (Na$_2$SO$_4$) and concentrated. The product was purified by column chromatography (silica gel) to yield compound 12 (0.69 g, 83%): MS (ES) m/z: 334 (MH$^+$).

Example 13

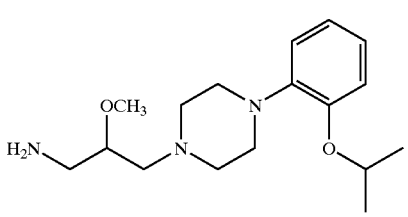
Cpd. 13

10%HCl (0.3 mL) was added to a mixture of compound 12 (0.64 g, 1.9 mmol) and 10% Pd/C (0.13 g) in MeOH (5 mL). This mixture was hydrogenated under $H_2$ (50 psi) in a Parr shaker overnight, filtered through celite and the filtrate was concentrated. The residue was basified with 20% NaOH and extracted with methylene chloride (3×), dried ($Na_2SO_4$) and concentrated to give a yellow oil at quantitative yield. MS (ES) m/z: 308 (MH⁺).

Example 14

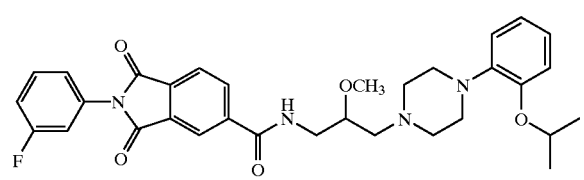
Cpd. 14

Compound 13 (0.15 g, 0.49 mmol) was dissolved in methylene chloride (4 mL) and 4 eq of diisopropylethyl amine (0.25 g, 1.95 mmol) was added. To this solution was added a mixture of HATU, (0.185 g, 0.49 mmol) and compound 3 (0.14 g, 0.49 mmol) and the reaction was stirred overnight under $N_2$ at RT. The solvent was evaporated and the product was purified by flash chromatography ($SiO_2$, methylene chloride/Acetone=10:1, 8:1, 6:1, 4:1, 2:1). The product was recrystallized from EtOAc/hexane to yield light yellow solid 0.08 g (29%): $^1$H NMR (300 MHz, CDCl$_3$) δ8.36 (m, 2H), 8.18 (brs, 1H), 8.02 (d, J=7.69 Hz, 1H), 7.47 (m, 1H), 7.22 (m, 3H), 7.00 (m, 1H), 6.87 (m, 3H), 4.57 (m, 1H), 3.76 (m, 3H), 3.50 (s, 3H), 3.22 (m, 10H), 1.35 (d, J=6.0 Hz, 6H); MS (ES) m/z: 575 (MH⁺).

Example 15

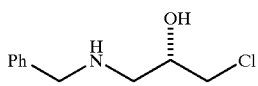
Cpd. 15

A mixture of (S)-(+)-epichlorohydrin (10 g, 108.1 mmol, Aldrich, 97% ee) and benzylamine (11.57 g, 108.1 mmol) in hexane (40 mL) were stirred at 20° C. for 62 h. White solid precipitated. More hexane (~350 mL) added, stirred for 20 min. and sonicated to break the big chunks of white solid. The white solid was collected by filtration and washed with hexane, dried under vacuum to give 19.8 g (92%) white solid. The white solid was recrystallized from EtOAc/hexane to give 17.76 g (82%) of 15 as a white crystalline solid; $^1$H NMR (300 MHz, CDCl$_3$) δ7.31 (m, 5H), 3.88 (m, 1H), 3.79 (m, 2H), 3.53 (d, J=5.3 Hz, 2H), 2.89 (m, 2H), 2.81 (dd, J=12.4, 4.1 Hz, 1H), 2.69 (dd, J=12.2, 7.9 Hz, 1H); MS (ES): 200 (MH⁺); Anal. Calcd. for $C_{10}H_{14}$NOCl: C, 60.15; H, 7.07; N, 7.01. Found: C, 60.10; H, 7.02; N, 6.92.

Example 16

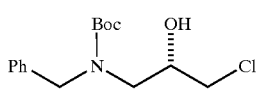
Cpd. 16

Boc$_2$O (11 g, 50.1 mmol) and triethylamine (10.12 g, 100 mmol) were dissolved in THF (25 mL) and cooled to 0° C. The amine 15 (10 g, 50.1 mmol) was added in portions and stirred for 20 h while the temperature was warmed up to 20° C. overnight. The solvent was concentrated in vacuo and water was added. The mixture was extracted with ether (3×), dried (Na$_2$SO$_4$) and concentrated. The crude residue was recrystallized from EtOAc/hexane to give 9.9 g (66%) of 16 as a white crystalline solid. The filtrate was concentrated (3.1 g as oil) and more product was purified by column chromatography (short column, 8 cm height of SiO$_2$, EtOAc/hexane as solvent). The oil was recrystallized from EtOAc/hexane to give another 2.78 g (18%) of 16 as a white crystaline solid; $[\alpha]_D^{25}$=−10.2° (c=1, CHCl$_3$); $^1$H NMR (300 MHz, CDCl$_3$) δ7.22–7.36 (m, 5H), 4.52 (m, 2H), 4.30 (brs, 0.5H), 3.96 (m, 1H), 3.36–3.97 (m, 4H), 1.47 (s, 9H); MS (ES): 322 (M+Na); Anal. Calcd. for $C_{15}H_{22}$NO$_3$Cl: C, 60.10; H, 7.40; N, 4.67. Found: C, 60.26, H, 7.42; N, 4.63

Example 17

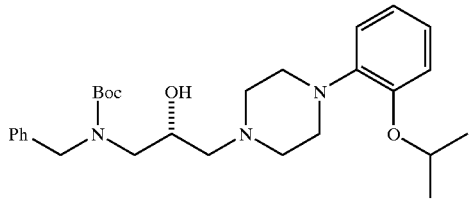
Cpd. 17

KOH (11.23 g, 200.5 mmol) was dissolved in methanol (280 mL), and the fumarate salt of 1-(2-isopropoxyphenyl)-piperazine (10.9 g, 33.4 mmol) was added and stirred at 20° C. for 20 min then cooled to 0° C. The Boc-protected amine 16 (10 g, 33.4 mmol) was added to the methanol solution at 0° C. and stirred for 20 h while the temperature was warm up to 20° C. overnight. The solvent was removed, water was added and the mixture was extracted with ether (3×), dried (Na$_2$SO$_4$) and concentrated. The product was purified by column chromatography (short column, 8 cm height SiO$_2$, EtOAc/hexane as solvent) to give 10.22 g (63%) of 17 (~100% ee, Chiralpak OD 4.6×250 mm. 1 mL/min, 254 nm, mobile phase: 90/10/0.1 of hexane/IPA/0.1% diethylamine) as a yellowish oil; $^1$H NMR (300 MHz, CDCl$_3$) δ7.26–7.35 (m, 5H), 6.91 (m, 4H), 4.68 (d, J=15.6 Hz, 1H), 4.59 (m, 3H), 3.95 (m, 1H), 3.35 (m, 2H), 3.11 (m, 4H), 2.75 (m, 2H), 2.54 (m, 2H), 2.38 (m, 2H), 1.45 (m, 9H), 1.34 (d, J=6.1 Hz, 6H); MS (ES): 484 (MH⁺).

Example 18

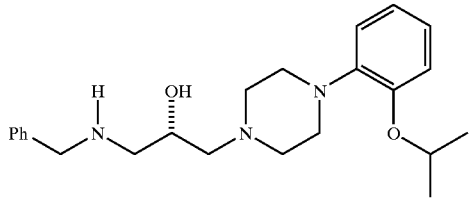
Cpd. 18

A mixture of compound 17 (233 mg, 0.48 mmol) and 25% TFA/methylene chloride (3 mL) was stirred at 20° C. for 18 h. The solvent was concentrated in vacuo and the residue was basified with 20% NaOH (aq), extracted with methylene chloride (3×), dried (Na$_2$SO$_4$) and concentrated to give 174 mg (~95%) of 18 as an oil which was used directly without further purification; MS (ES): 384 (MH$^+$).

Example 19

Alternative Preparation of Cpd. 8

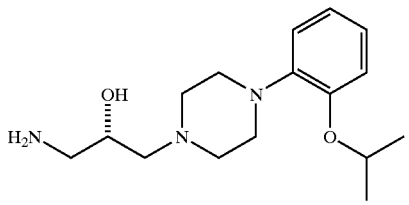
Cpd. 19

To a mixture of 18 (~154 mg, 0.4 mmol) and 10% Pd/C (154 mg) in EtOH (3 mL) was added ammonium formate (151 mg, 2.4 mmol) and stirred at 55–60° C. for 20 h. The mixture was filtered thru celite and washed with methanol. The filtrate was concentrated. The product was purified by a short column (5 cm height of SiO$_2$) to give 63 mg (54%) of 19 as a oil; [α]$_D^{25}$+23.6° (c=1, CHCl$_3$); $^1$H NMR (300 MHz, CDCl$_3$) δ6.91 (m, 4H), 4.59 (m, 1H), 3.76 (m, 1H), 3.12 (m, 4H), 2.83 (dd, J=12.7, 3.7 Hz, 2H), 2.82 (m, 1H), 2.25–2.68 (m, 8H), 1.34 (d, J=6.1 Hz, 6H); MS (ES): 294 (MH$^+$).

Example 20

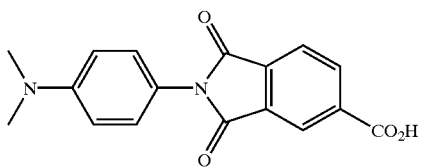
Cpd. 20

A mixture of the 1,2,4-benzenetricarboxylic anhydride (7 g, 36.4 mmol), and N,N-dimethyl-1,4-phenylenediamine (4.96 g, 36.4 mmol) in glacial acidic acid (120 mL) was stirred at 130° C. for 16 h. The reaction solution was cooled to 20° C. and light brown solid precipitated out. The solid was collected thru filtration and was washed thoroughly with water to remove the trace amount of acetic acid. The product was dried at 40° C. for 36 h under vacuum to yield 8.0 g (71%) of 20 as a light brown solid: $^1$H NMR (300 MHz, DMSO-d$_6$) δ8.40 (d, J=8.5 Hz, 1H), 8.28 (s, 1H), 8.05 (d, J=7.8 Hz, 1H), 7.22 (d, J=8.9 Hz, 2H), 6.82 (d, J=8.9 Hz, 2H), 2.96 (s, 6H); MS (ES): 309 (MH$^+$).

Example 21

(S)-2-[4-(dimethylamino)phenyl]-2,3-dihydro-N-[2-hydroxy-3-[4-[2-(1-methylethoxy)phenyl]-1-piperazinyl]propyl]-1,3-dioxo-1H-isoindole-5-carboxamide Cpd. 21

The piperazine 19 (0.4 g, 1.36 mmol) was dissolved in a mixture of diisopropylethyl amine (0.7 g, 5.46 mmol) and methylene chloride (10 mL). To the above solution was added compound 20 (420 mg, 1.36 mmol) and HATU (0.52 g, 1.36 mmol) and stirred at 20° C. for 18 h. The reaction mixture was washed with 3% K$_2$CO$_3$ (aq) and the organic layer was dried (Na$_2$SO$_4$), and concentrated. The product was purified by column chromatography (SiO$_2$, CH$_2$Cl$_2$/Acetone=10:1, 8:1, 6:1, 4:1, 2:1) to give 0.33 g (41%) of cpd. 21 as a light brown solid: $^1$H NMR (300 MHz, CDCl$_3$) δ8.27 (m, 2H), 8.00 (d, J=7.7 Hz, 1H), 7.23 (s, 1H), 6.90 (m, 5H), 6.79 (d, J=8.9 Hz, 2H), 4.59 (m, 1H), 4.00 (m, 1H), 3.83 (m, 1H), 3.44 (m, 1H), 3.12 (brs, 4H), 3.00 (s, 6H), 2.85 (m, 2H), 2.52 (m, 4H) 1.34 (d, J=6.1 Hz, 6H); MS (ES): 586 (MH$^+$) [α]$_D^{25}$=9.6°(C=0.2, CHCl$_3$)

Biological Examples

The biological activity and selectivity of the compounds of the invention was demonstrated by the following assays. The first assay tested the ability of compounds of Formula I to bind to membrane bound receptors α1$_a$-AR, α1$_b$-AR and α1$_d$-AR.

Example 22

The DNA sequences of the three cloned human α1-AR subtypes have been published. Furthermore, the cloned cDNAs have been expressed both transiently in COS cells and stably in a variety of mammalian cell lines (HeLa, LM(tk-), CHO, rat-1 fibroblast) and have been shown to retain radioligand binding activity and the ability to couple to phosphoinositide hydrolysis. We used published DNA sequence information to design primers for use in RT-PCR amplification of each subtype to obtain cloned cDNAs. Human poly A+ RNA was obtained from commercially available sources and included hippocampus and prostate samples, sources which have been cited in the literature. For the primary screen a radioligand binding assay was used which employed membrane preparations from cells expressing the individual cloned receptor cDNAs. Radiolabeled ligands with binding activity on all three subtypes (non-selective) are commercially available ([125I]-HEAT, [3H]-prazosin). Each α1 receptor subtype was cloned from poly A+ RNA by the standard method of reverse transcription-polymerase chain reaction (RT-PCR). The following sources of polyA+ RNA were used for the cloning of the α1 receptor subtypes: α1$_a$-AR, human hippocampus and prostate, α1$_b$-AR, human hippocampus, α1$_d$-AR, human hippocampus. The resulting cDNAs were cloned into the pcDNA3 mammalian expression vector (Invitrogen Corp., San Diego Calif.). Each DNA was sequenced for verification and to detect any possible mutations introduced during the ampli-

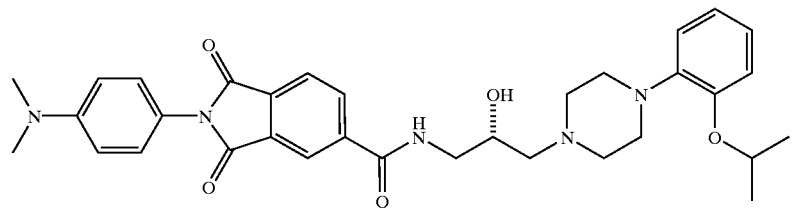

fication process. Any deviation in sequence from the published consensus for each receptor subtype was corrected by site-directed mutagenesis.

The three α1-AR subtypes (a, b, d) were transfected into COS cells using a standard DEAE-dextran procedure with a chloroquine shock. In this procedure, each tissue culture dish (100 mm) was inoculated with $3.5 \times 10^6$ cells and transfected with 10 μg of DNA. Approximately 72 hours post-transfection, the cells were harvested and COS membranes were prepared. Transfected COS cells from 25 plates (100 mm) were scraped and suspended in 15 mL of TE buffer (50 mM Tris-HCl, 5 mM EDTA, pH 7.4). The suspension was disrupted with a homogenizer. It was then centrifuged at 1000× g for 10 minutes at 4° C. The supernatant was centrifuged at 34,500× g for 20 minutes at 4° C. The pellet was resuspended in 5 mL TNE buffer (50 mM Tris-HCl, 5 mM EDTA, 150 mM NaCl, pH 7.4). The resulting membrane preparation was aliquoted and stored at −70° C. The protein concentration was determined following membrane solubilization with TritonX-100.

The ability of each compound to bind to each of the α1-AR subtypes was assessed in a receptor binding assay. [125I]-HEAT, a non-selective α1-AR ligand, was used as the radiolabeled ligand. Each well of a 96-well plate received: 140 μL TNE, 25 mL [125I]-HEAT diluted in TNE (50,000 cpm; final concentration 50 pM), 10 μL test compound diluted in DMSO (final concentration 1 pM-10 μM), 25 mL COS cell membrane preparation expressing one of the three α1-AR subtypes (0.05–0.2 mg membrane protein). The plate was incubated for 1 hour at room temperature and the reaction mixtures were filtered through a Packard GF/C Unifilter filter plate. The filter plate was dried for 1 hour in a vacuum oven. Scintillation fluid (25 mL) was added to each well, and the filter plate was counted in a Packard Topcount scintillation counter. Data was analyzed using GraphPad Prism software.

Tables A through D list the $IC_{50}$ values expressed in nanomolar concentration for select compounds of the invention in all receptor subtypes.

TABLE A

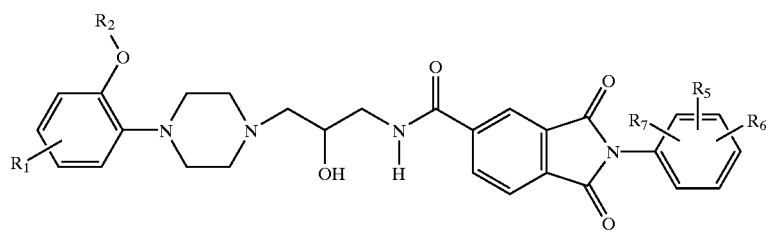

| Cpd. | $R_1$ | $R_2$ | $R_5$ | $R_6$ | $R_7$ | α1a | α1b | α1d |
|---|---|---|---|---|---|---|---|---|
| 4 | H | i-propyl | 3-F | H | H | 1.5 | 1835 | 76 |
| 48 | H | i-propyl | 4-acetyl | H | H | 1.0 | >2000 | 60 |
| 49 | H | i-propyl | 3-$CH_3$ | H | H | 0.9 | >2000 | 73 |
| 50 | H | i-propyl | 4-F | H | H | 1.5 | >2000 | 111 |
| 51 | H | i-propyl | H | H | H | 0.9 | >2000 | 65 |
| 52 | H | i-propyl | 4-$CH_3$ | H | H | 0.66 | >2000 | 62 |
| 53 | H | i-propyl | 4-Cl | H | H | 0.95 | 606 | 55 |
| 54 | H | i-propyl | 3-Cl | H | H | 0.73 | 669 | 37 |
| 55 | H | i-propyl | 4-$OCH_3$ | H | H | 0.77 | >2000 | 51 |
| 56 | H | i-propyl | 3-Cl | 4-Cl | H | 0.81 | 1225 | 40 |
| 57 | H | i-propyl | 3-$CF_3$ | H | H | 0.74 | >2000 | 89 |
| 58 | H | i-propyl | 4-OH | H | H | 0.88 | >2000 | 28 |
| 26 | H | i-propyl | 2-$OCH_3$ | H | H | 1.6 | 1639 | 74 |
| 27 | H | i-propyl** | 3-F | H | H | 8 | >2000 | 63 |
| 9 | H | i-propyl* | 3-F | H | H | 1.0 | >2000 | 190 |
| 28 | H | i-propyl | 4-$N(CH_3)_2$ | H | H | 0.80 | >2000 | 44 |
| 29 | H | i-propyl | 3-F | 5-F | H | 0.89 | 886 | 38 |
| 30 | H | i-propyl | 4-$NO_2$ | H | H | 1.8 | >2000 | 38 |
| 31 | H | i-propyl** | 4-$OCH_3$ | H | H | 2.2 | >2000 | 52 |
| 32 | H | i-propyl* | 4-$OCH_3$ | H | H | 0.23 | 1750 | 124 |
| 21 | H | i-propyl* | 4-$N(CH_3)_2$ | H | H | 0.36 | >2000 | 52 |
| 34 | H | i-propyl* | 4-$CH_3$ | H | H | 0.16 | 1650 | 37 |
| 35 | H | i-propyl* | 4-OH | H | H | 0.46 | >2000 | 137 |
| 36 | H | i-propyl* | 2-$OCH_3$ | H | 4-$OCH_3$ | 0.59 | >2000 | 56 |
| 37 | H | i-propyl* | 5-$OCH_3$ | 3-$OCH_3$ | 4-$OCH_3$ | 0.62 | >2000 | 51 |
| 38 | H | i-propyl* | H | 3-$OCH_3$ | 4-$OCH_3$ | 0.93 | >2000 | 175 |
| 39 | H | i-propyl | H | 3-$CH_3$ | -4-$CH_3$ | 0.44 | >2000 | 73 |
| 40 | H | i-propyl* | H | 3-$CH_3$ | -4-$CH_3$ | 0.26 | >2000 | 121 |
| 41 | H | i-propyl | H | H | 4-t-butyl | 3.5 | >2000 | 75 |
| 42 | H | ethyl | 3-F | H | H | 4.25 | >2000 | 136 |
| 43 | H | methyl | 3-F | H | H | 22 | >2000 | 540 |

*indicates "S" stereochemistry
**indicates "R" stereochemistry

TABLE B

| RWJ | $R_1$ | $R_2$ | $R_5$ | $R_6$ | $R_7$ | α1a | α1b | α1d |
|---|---|---|---|---|---|---|---|---|
| 6 | H | i-propyl | 3-F | H | H | 0.41 | 482 | 22 |
| 44 | H | i-propyl | H | H | 4-N(CH$_3$)$_2$ | 0.18 | 465 | 15 |
| 45 | H | i-propyl | H | H | 4-OCH$_3$ | 0.11 | 361 | 16 |
| 46 | H | i-propyl | H | H | 4-CH$_3$ | 0.1 | >2000 | 37 |
| 47 | H | i-propyl | H | H | 4-OH | 0.2 | 255 | 13 |

TABLE C

| Cpd. | $R_1$ | $R_2$ | $R_5$ | $R_6$ | $R_7$ | α1a | α1b | α1d |
|---|---|---|---|---|---|---|---|---|
| 11 | H | i-propyl | H | H | H | 1.9 | >2000 | 31 |

TABLE D

| Cpd. | $R_1$ | $R_2$ | $R_5$ | $R_6$ | $R_7$ | α1a | α1b | α1d |
|---|---|---|---|---|---|---|---|---|
| 14 | H | i-propyl | 3-F | H | H | 7 | >2000 | 407 |

Example 23

The selectivity of the compounds of the invention for prostate tissues over aortic tissues was demonstrated as follows. The contractile responses of rat prostatic tissue and rat aorta tissues were examined in the presence and absence of antagonist compounds. As an indication of the selectivity of antagonism, test compound effects on vascular smooth muscle contractility (α1$_b$-AR and α1$_d$-AR) were compared to the effects on prostatic smooth muscle (α1$_a$-AR). Strips of prostatic tissue and aortic rings were obtained from Long Evans derived male rats weighing 275 grams and sacrificed by cervical dislocation. The prostate tissue was placed under 1 gram tension in a 10 ml bath containing phosphate buffered saline pH 7.4 at 32° C. and isometric tension was measured with force transducers. The aortic tissue was placed under 2 grams tension in a 10 ml bath containing phosphate buffered saline pH 7.4 at 37° C. The ability of test compound to reduce the norepinephrine-induced contractile response by 50% (IC$_{50}$) was determined. Compound 4 inhibited the contractile response in aortic tissue with an IC$_{50}$ of 63.2 μM and in prostate tissue with an IC$_{50}$ of 0.64 μM. Compound 6 inhibited the contractile response in aortic tissue with an IC$_{50}$ of 2.8 μM and in prostate tissue with an IC$_{50}$ of 0.13 μM. Compound 9 inhibited the contractile response in aortic tissue with an IC$_{50}$ of 6.5 μM and in prostate tissue with an IC$_{50}$ of 0.23 μM. Compound 45 inhibited the contractile response in aortic tissue with an IC$_{50}$ of 3.3 μM and in prostate tissue with an IC$_{50}$ of 0.04 μM. Compound 34 inhibited the contractile response in aortic tissue with an IC$_{50}$ of 42.5 μM and in prostate tissue with an IC$_{50}$ of 0.75 μM. Compound 21 inhibited the contractile response in aortic tissue with an IC$_{50}$ of 22.4 µM and in prostate tissue with an IC$_{50}$ of 0.81 µM.

Example 24

Select compounds of the invention were tested for their ability to antagonize phenylephrine (PE) induced increases in intraurethral pressure in dogs. The selectivity of these compounds was demonstrated by comparing their effect upon PE induced increases in mean arterial pressure (MAP) in the dog.

Figure 2:
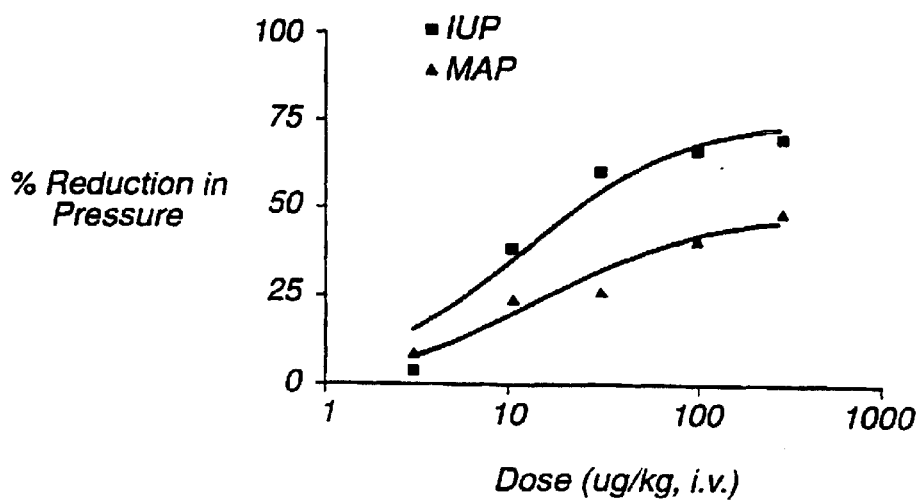
FIG. 2 is a graph of the effect of Compound 46 on the reduction of IUP and MAP responses in dogs.

Male beagle dogs were anesthetized and catheterized to measure intraurethral pressure (IUP) in the prostatic urethra. Mean arterial pressure (MAP) was measured using a catheter placed in the femoral artery. Dogs were initially administered six i.v. bolus doses (1 to $\leq$32 mg/kg) of phenylephrine (PE) to establish a control agonist dose-response curve. IUP and MAP were recorded following each dose until the IUP returned to baseline. The dogs then were given an i.v. bolus dose of the antagonist compound, followed by i.v. PE challenges of ascending doses, as in the control agonist dose-response curve. IUP and MAP measurements following each PE challenge were recorded. The antagonist compound was tested over a dose range of 3 to 300 ug/kg in half-log increments. The interval between antagonist doses was at least 45 min and three experiments were performed for each test compound. FIGS. 1 and 2 illustrates the mean percentage reductions in IUP and MAP for compounds 21 and 46 respectively.

Example 25

Figure 3:
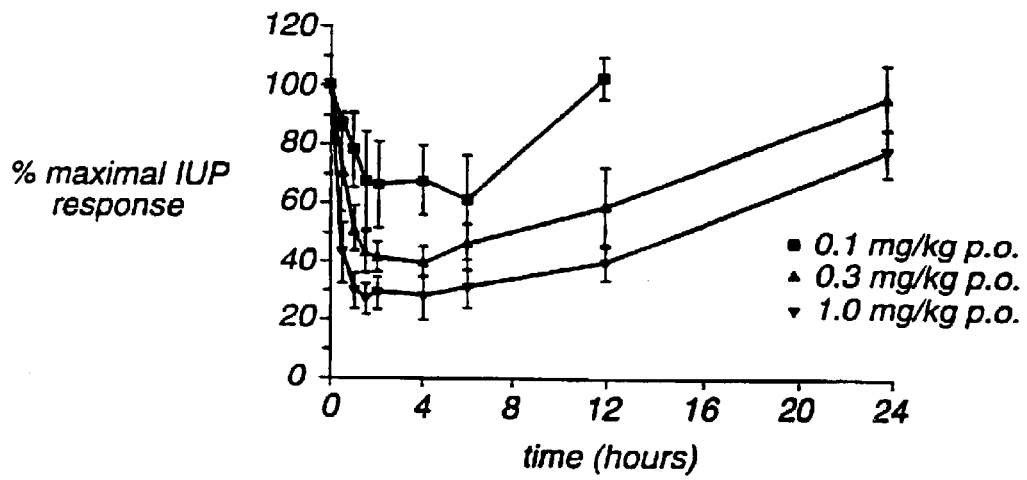
FIG. 3 is a graph of the effect of Compound 21 on IUP response.
Figure 4:
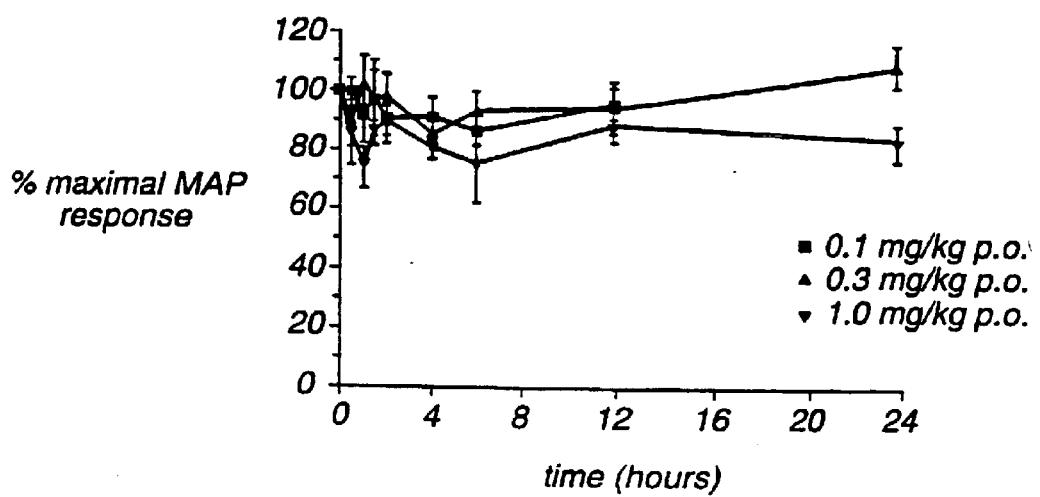
FIG. 4 is graph of the effect of Compound 21 on MAP response.

The duration of select compounds of the invention was determined by the measuring the IUP and MAP responses to repeated PE challenges in conscious dogs over time. Male beagles dogs were instrumented for the continuous measurement of arterial blood pressure by implanting a catheter containing a pressure transducer into the abdominal aorta via the femoral artery. The telemetry transmitter was positioned subcutaneously in the animal's flank. IUP was monitored with a catheter positioned in the prostatic urethra. Prior to antagonist test compound administration, the IUP and MAP responses to a 20 µg/kg i.v. dose of PE were determined and repeated several times to establish a baseline (100% maximal) response. An oral bolus dose of antagonist was administered, followed by a 20 µg/kg i.v. PE challenge at 0.5, 1, 1.5, 2, 4, 6, 12, and 24 hours post dosing. The IUP and MAP responses following each PE challenge were recorded. Compound 21 was tested at doses of 0.1, 0.3, and 1 mg/kg. The IUP and MAP responses at each time point following the PE challenge are presented in FIGS. 3 and 4 as the percent of the maximal response.

REFERENCES

M. Barry & C. Roehborn, Management of Benign Prostatic Hyperplasia, 48 Annu. Rev. Med. 177–89 (1997), Bruno J F, Whittaker J, Song J, and Berelowitz M. (1991) Molecular cloning and sequencing of a cDNA encoding a human α1A adrenergic receptor. Biochem. Biophys. Res. Commun. 179: 1485–1490.

Forray C, Bard J A, Wetzel J M, Chiu G, Shapiro E, Tang R, Lepor H, Hartig P R, Weinshank R L, Branchek T A, and Gluchowski C (1994) The α1-adrenergic receptor that mediates smooth muscle contraction in human prostate has the pharmacological properties of the cloned human α1c subtype. Mol. Pharmacol. 45: 703–708.

Gormley G, Stoner E, Bruskewitz R C et al. (1992) The effect of finasteride in men with benign prostatic hyperplasia. N. Engl. J. Med. 327: 1185–1191.

Hatano A, Takahashi H, Tamaki M, Komeyama T, Koizumi T, and Takeda M (1994) Pharmacological evidence of distinct α1-adrenoceptor subtypes mediating the contraction of human prostatic urethra and peripheral artery. Br. J. Pharmacol. 113: 723–728.

Harrison J K, Pearson W R, and Lynch K R (1991) Molecular characterization of α1- and α2-adrenoceptors. Trends Pharmacol. Sci. 12: 62–67.

Hieble J P and Caine M (1986) Etiology of benign prostatic hyperplasia and approaches to pharmacological management. Fed. Proc. 45: 2601–2603.

Hirasawa A, Horie K, Tanaka T, Takagaki K, Murai M, Yano J, and Tsujimoto G (1993) Cloning, functional expression and tissue distribution of human cDNA for the α1 c-adrenergic receptor. Biochem. Biophys. Res. Commun. 195: 902–909.

Lepor H and Rigaud G (1990) The efficacy of transurethral resection of the prostate in men with moderate symptoms of prostatism. J. Urol. 143: 533–537.

Lepor H, Auerbach S, Puras-Baez A et al. (1992) A randomized, placebo-controlled multicenter study of the efficacy and safety of terazosin in the treatment of benign prostatic hyperplasia. J. Urol. 148: 1467–1474.

Lepor H (1995) α-Blockade for benign prostatic hyperplasia (BPH) J. Clin. Endocrinol. Metab. 80: 750–753.

Marshall I, Burt R P, Andersson P O, Chapple C R, Greengrass P M, Johnson G I, and Wyllie M G (1992) Human α1c-adrenoceptor: functional characterisation in prostate. Br. J. Pharmacol. 107(Proc. Suppl. Dec.):327P.

Marshall I, Burt R P, and Chapple C R (1995) Noradrenaline contractions of human prostate mediated by α1A—(α1c-) adrenoceptor subtype. Br. J. Pharmacol. 115: 781–786.

Mebust W K, Holtgrewe H L, Cockett A T K, and Peters P C (1989) Transurethral prostatectomy: immediate and postoperative complications. A cooperative study of 13 participating institutions evaluating 3,885 patients. J. Urol., 141: 243–247.

Oesterling J E (1995) Benign prostatic hyperplasia. Medical and minimally invasive treatment options. N. Engl. J. Med. 332: 99–109.

Ramarao C S, Kincade Denker J M, Perez D M, Gaivin R J, Riek R P, and Graham R M (1992) Genomic organization and expression of the human α1B-adrenergic receptor. J. Biol. Chem. 267: 21936–21945.

Schwinn D A, Johnston G I, Page S O, Mosley M J, Wilson K H, Worman N P, Campbell S, Fidock M D, Furness L M, Parry-Smith D J, Peter B, and Bailey D S (1995) Cloning and pharmacological characterization of human alpha-1 adrenergic receptors: sequence corrections and direct comparison with other species homologues. JPET 272: 134–142.

William D. Steers & Burkhart Zorn, Benign Prostatic Hyperplasia, in Disease-a-Month (M. Greenbeerger et al. Eds., 1995).

Weinberg D H, Trivedi P, Tan C P, Mitra S, Perkins-Barrow A, Borkowski D, Strader C D, and Bayne M (1994) Cloning, expression and characterization of human α adrenergic receptors α1A, α1B, and α1C. Biochem. Biophys. Res. Commun. 201: 1296–1304.

Weis K A, Epstein R S, Huse D M, Deverka P A and Oster G (1993) The costs of prostatectomy for benign prostatic hyperplasia. Prostate 22: 325–334.

Wennberg J E, Roos N, Sola L, Schori A, and Jaffe R (1987) Use of claims data systems to evaluate health care outcomes: mortality and reoperation following prostatectomy. JAMA 257: 933–936.

Yamada S, Tanaka C, Kimura R, and Kawabe K (1994) Alpha 1-adrenoceptors in human prostate: characterization and binding characteristics of alpha 1-antagonists. Life Sci. 54: 1845–1854.

What is claimed is:

1. A method of making a compound of Formula II

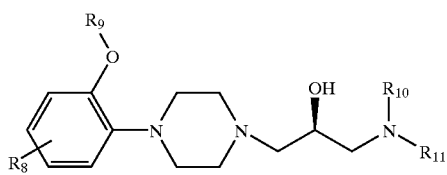

wherein
$R_8$ is hydrogen;
$R_9$ is $C_{3-6}$alkyl, or substituted $C_{3-6}$alkyl
where the alkyl substituents are independently selected from one or more halogens;
$R_{10}$ is hydrogen;
$R_{11}$ is hydrogen
comprising
reacting a compound of Formula II
wherein
$R_8$ is hydrogen;
$R_9$ is $C_{3-6}$alkyl, or substituted $C_{3-6}$alkyl
where the alkyl substituents are independently selected from one or more halogens;
$R_{10}$ is hydrogen;
$R_{11}$ is benzyl, or substituted benzyl
where the benzyl substituents are independently selected from one or more members of the group consisting of $C_{1-5}$alkyl, halogen, $C_{1-5}$alkoxy, and nitro;
with a reducing agent to give a compound of Formula II
wherein
$R_8$ is hydrogen;
$R_9$ is $C_{3-6}$alkyl, or substituted $C_{3-6}$alkyl
where the alkyl substituents are independently selected from one or more halogens,
$R_{10}$ is hydrogen;
$R_{11}$ is hydrogen.

2. The method of claim 1 wherein $R_8$ is hydrogen and $R_9$ is isopropyl.

3. The method of claim 1 wherein the reducing agent is ammonium formate and Pd/C.

* * * * *